US010246684B2

(12) United States Patent
Kanbara et al.

(10) Patent No.: US 10,246,684 B2
(45) Date of Patent: Apr. 2, 2019

(54) CANCER CELL-TRAPPING METAL FILTER, CANCER CELL-TRAPPING METAL FILTER SHEET, CANCER CELL-TRAPPING DEVICE, AND MANUFACTURING METHODS THEREFOR

(71) Applicant: HITACHI CHEMICAL COMPANY, LTD., Tokyo (JP)

(72) Inventors: Hisashige Kanbara, Oyama (JP); Yoshihito Kikuhara, Oyama (JP); Takahiro Suzuki, Oyama (JP)

(73) Assignee: HITACHI CHEMICAL COMPANY, LTD., Tokyo (JP)

( * ) Notice: Subject to any disclaimer, the term of this patent is extended or adjusted under 35 U.S.C. 154(b) by 59 days.

(21) Appl. No.: 15/465,638

(22) Filed: Mar. 22, 2017

(65) Prior Publication Data
US 2017/0247662 A1 Aug. 31, 2017

Related U.S. Application Data

(62) Division of application No. 14/400,022, filed as application No. PCT/JP2013/063163 on May 10, 2013, now abandoned.

(30) Foreign Application Priority Data

May 14, 2012 (JP) ................................ 2012-110898

(51) Int. Cl.
*B01D 39/10* (2006.01)
*G03F 7/42* (2006.01)
(Continued)

(52) U.S. Cl.
CPC ........... *C12N 5/0694* (2013.01); *B01D 39/10* (2013.01); *B22D 25/02* (2013.01); *B22D 29/00* (2013.01);
(Continued)

(58) Field of Classification Search
CPC ..... C12N 5/0694; G03F 7/038; G03F 7/2004; G03F 7/039; G03F 7/428; G03F 7/405;
(Continued)

(56) References Cited

U.S. PATENT DOCUMENTS

| 4,740,303 A | 4/1988 | Greutert et al. |
| 2004/0129630 A1* | 7/2004 | Baker ................... B01D 29/03 210/499 |

FOREIGN PATENT DOCUMENTS

| CN | 1781020 | 5/2006 |
| DE | 3441970 | 2/1986 |

(Continued)

OTHER PUBLICATIONS

CN Office Action of Appln. No. 201380024989.3 dated Jun. 17, 2015.
(Continued)

*Primary Examiner* — Madeline Gonzalez
(74) *Attorney, Agent, or Firm* — Fitch, Even, Tabin & Flannery, LLP

(57) ABSTRACT

Provided are a cancer cell-trapping metal filter which has a high opening ratio, a cancer cell-trapping metal filter sheet, a cancer cell-trapping device using the cancer cell-trapping filter, and manufacturing methods therefor.
According to a cancer cell-trapping metal filter 1, openings of connected through-holes 12 that are formed in a metal sheet 11 have a wave shape, and thus it is possible to extract a CTC from other components by utilizing a hole diameter on a short-side side of the openings, and it is possible to make the connected through-holes be closer to each other due to the wave shape while maintaining a CTC trapping ability. Accordingly, it is possible to further improve the opening ratio in the cancer cell-trapping metal filter 1.

15 Claims, 17 Drawing Sheets

(51) Int. Cl.

| | | |
|---|---|---|
| *C12N 5/09* | (2010.01) | |
| *G01N 33/49* | (2006.01) | |
| *B22D 25/02* | (2006.01) | |
| *B22D 29/00* | (2006.01) | |
| *G01N 1/40* | (2006.01) | |
| *C08J 5/12* | (2006.01) | |
| *G03F 7/038* | (2006.01) | |
| *G03F 7/039* | (2006.01) | |
| *G03F 7/20* | (2006.01) | |
| *G03F 7/32* | (2006.01) | |
| *G03F 7/40* | (2006.01) | |

(52) U.S. Cl.
CPC ............ *C08J 5/121* (2013.01); *G01N 1/4077* (2013.01); *G01N 33/49* (2013.01); *G03F 7/038* (2013.01); *G03F 7/039* (2013.01); *G03F 7/2004* (2013.01); *G03F 7/322* (2013.01); *G03F 7/405* (2013.01); *G03F 7/428* (2013.01); *C08J 2300/12* (2013.01); *G01N 2001/4088* (2013.01); *Y10T 29/49* (2015.01); *Y10T 156/10* (2015.01)

(58) Field of Classification Search
CPC ....... G03F 7/322; C08J 5/121; C08J 2300/12; B22D 29/00; B22D 25/02; G01N 1/4077; G01N 33/49; G01N 2001/4088; B01D 39/10; Y10T 29/49; Y10T 156/10
USPC .................................................. 210/498, 232
See application file for complete search history.

(56) References Cited

FOREIGN PATENT DOCUMENTS

| EP | 2720039 | 4/2014 |
|---|---|---|
| JP | 7-051521 | 2/1995 |
| JP | 2006-193825 | 7/2006 |
| JP | 2007-178366 | 7/2007 |
| JP | 2011-163830 | 8/2011 |
| JP | 2013-042689 | 3/2013 |
| WO | 2010/135603 | 11/2010 |
| WO | 2011/139233 | 11/2011 |
| WO | 2011/139445 | 11/2011 |
| WO | 2013/103144 | 7/2013 |

OTHER PUBLICATIONS

Search Report of EP Appln. No. 13791257.2 dated Nov. 24, 2015 in English.
Office Action of JP Patent Application No. P2013-100466 dated Nov. 8, 2016.
Hosokawa et al., Development of Microfluidic Device for Rapid Detection of Circulating Tumor Cells, Chemical Sensors, 2010, vol. 26, Suppl. B, pp. 40-42 with partial translation.
Yoshikawa et al., Optimization of Microfilter Structure for Enrichment of Circulating Tumor Cells from Whole Blood, Dai 63 Kai Abstracts of the Annual meeting of the Society for Biotechnology, Japan, 2011, p. 201 2Lp11 with translation.
International Search Report of Appln. No. PCT/JP2013/063163 dated Aug. 13, 2013 in English.
International Preliminary Report of Appln. No. PCT/JP2013/063163 dated Nov. 27, 2014 in English.
Office Action of U.S. Appl. No. 14/400,022 dated Mar. 31, 2017.

* cited by examiner

CANCER CELL-TRAPPING METAL FILTER, CANCER CELL-TRAPPING METAL FILTER SHEET, CANCER CELL-TRAPPING DEVICE, AND MANUFACTURING METHODS THEREFOR

CROSS-REFERENCE TO RELATED APPLICATIONS

This application is a divisional application of U.S. application Ser. No. 14/400,022 filed Nov. 10, 2014, which is a 371 of International Application No. PCT/JP2013/063163, filed May 10, 2013, which claims priority to JP2012-110898, filed May 14, 2012, the contents of each of which are incorporated herein by reference.

TECHNICAL FIELD

The present invention relates to a cancer cell-trapping metal filter, a cancer cell-trapping metal filter sheet, and a cancer cell-trapping device which are capable of efficiently trapping a circulating tumor cell (hereinafter, may be referred to as a "CTC"), and manufacturing methods therefor.

BACKGROUND ART

The CTC is defined as a tumor cell that circulates through a human peripheral blood flow, and is tumor cell that infiltrates into a blood vessel from a primary cell or a metastatic tumor. If the CTC can be trapped in the same state as that in a blood flow, early detection of cancer or early development of effective medicine can be expected. However, the number of CTCs as small as one per 108 to 109 blood cells included in blood of a metastatic cancer patient, and thus it is difficult to trap only the CTC except for blood cells.

In consideration of the difficulty, a method of separating a blood cell and a cancer cell by utilizing a difference in size between the blood cell and the cancer cell has been examined (for example, refer to Patent Literature 1). In this method, a metal filter is used, and thus a variation in hole size is small. Accordingly, separation of the cancer cell with high separation accuracy and concentration thereof have been expected (for example, refer to Patent Literature 2).

The metal filter disclosed in Patent Literature 2 has a rectangular hole shape, and is typically formed by electro-deposition, electro-casting, or plating using a resist. In a case of manufacturing the metal filter by this method, a plurality of resist islands for formation of a through-hole of the filter are arranged on a substrate to be close to each other on a substrate in the middle of a manufacturing process. Here, when a rinsing liquid flows through a narrow space between resists, a problem such as collapse of a resist pattern formed in an island shape and peeling-off of the resist pattern from the substrate occurs, and thus there is a problem in that a yield ratio of the metal filter decreases. In addition, similarly, trapping of the CTC by using a metal filter manufactured by the electro-casting is examined (for example, refer to Patent Literature 3).

CITATION LIST

Patent Literature

[Patent Literature 1] PCT International Publication No. WO2010/135603

[Patent Literature 2] Japanese Unexamined Patent Application Publication No. H7-51521

[Patent Literature 3] Japanese Unexamined Patent Application Publication No. 2011-163830

SUMMARY OF INVENTION

Technical Problem

Recently, in a field of metastatic cancer, utility of the CTC as a determination and prediction factor of an early treatment effect, and a prognosis predictive factor is recognized. Therefore, it is preferable to improve accuracy in CTC measurement, and thus it is preferable to provide a filter having a high opening ratio so as to improve separation accuracy of the CTC. Patent Literature 3 discloses a metal filter formed by using an electrocuting technology, and discloses a structure in which a resist pattern is less likely to collapse from a structural aspect. However, in the metal filter disclosed in Patent Literature 3, it is difficult to shorten a distance between through-holes adjacent to each other from a structural aspect, and thus it is difficult to obtain high opening ratio.

The invention has been made in consideration of the above-described situations, and an object thereof is to provide a cancer cell-trapping metal filter which has a high opening ratio and is produced with high production efficiency, a cancer cell-trapping metal filter sheet, a cancer cell-trapping device using the cancer cell-trapping metal filter, and manufacturing methods therefor.

Solution to Problem

To accomplish the above-described object, according to an aspect of the invention, there is provided a cancer cell-trapping metal filter having a through-hole that is formed in a thickness direction of a metal sheet in which a main component is composed of a metal. An opening of the through-hole has a wave shape.

As described above, the opening of the through-hole has the wave shape, and thus it is possible to extract a CTC from other components by utilizing a hole diameter on a short-side side (hereinafter, a length on the short-side side is referred to as "hole diameter" for convenience and definition of the hole diameter will be described later), and it is possible to make through-holes be closer to each other due to the wave shape while maintaining a CTC trapping ability. Accordingly, it is possible to further improve an opening ratio in the cancer cell-trapping metal filter.

Here, as a configuration capable of effectively obtaining the above-described operation, specifically, it preferable that a plurality of the through-holes be arranged. When the plurality of through-holes are arranged, it is possible to dispose the plurality of through-holes in a state of being closer to each other, and thus it is possible to effectively improve the opening ratio.

Here, it is preferable that the opening ratio of the opening be 10% to 50%. When the opening ratio is set in the above-described range, it is possible to attain handing easiness as a filter or an improvement in a yield ratio while maintaining a CTC trapping ability due to the metal filter.

In addition, it is preferable that a surface of the metal sheet be plated with gold. When the surface of the metal sheet is plated with gold, adhesiveness of a CTC and blood cell components with respect to the filter becomes constant, and thus it is possible to raise reproducibility of data.

In addition, according to another aspect of the invention, there is provided a cancer cell-trapping metal filter sheet including a plurality of filtration portions having a through-hole formed in a thickness direction of a metal sheet in which a main component is composed of a metal, and a connection portion that is provided between two adjacent filtration portions that are included in the plurality of filtration portions. A plurality of the through-holes, which have a wave-shaped opening, are formed in the filtration portion.

As described above, the opening of the through-holes provided in the filtration portion has a wave shape, and thus it is possible to extract the CTC from other components by utilizing the hole diameter on a short-side side, and it is possible to make through-holes be closer to each other due to the wave shape while maintaining the CTC trapping ability. Accordingly, it is possible to further improve the opening ratio in the cancer cell-trapping metal filter sheet.

Here, it is preferable that the opening ratio of the opening in the filtration portion be 10% to 50%.

In addition, it is preferable that a positioning hole be formed in the connection portion. When the positioning hole is provided separately from the through-hole, it is possible to make attachment easy when constituting a cancer cell-trapping device by using the cancer cell-trapping metal filter sheet.

In addition, according to still another aspect of the invention, there is provided a cancer cell-trapping device including a casing that includes a cover member which is formed from a light-transmitting resin material and which has an inlet channel from which a liquid to be tested is introduced to the inside of the casing, and an accommodation member that has an outlet channel through which the liquid to be tested is discharged to the outside of the casing, and the above-described cancer cell-trapping metal filter which is provided on a flow path inside the casing between the inlet channel and the outlet channel in such a manner that the liquid to be tested flows through the through-hole.

Here, it is preferable that a hole diameter of the through-hole in a main surface on an upstream side be smaller than a hole diameter on a rear surface side with respect to the main surface. According to this aspect, it is possible to avoid staying of a material, which passes through the through-hole from an upstream side, in the through-hole, and thus it is possible to prevent clogging of the filter, and the like.

In addition, it is preferable that instead of the cancer cell-trapping metal filter, a cancer cell-tapping metal filter member, which includes a filtration portion having a through-hole formed in a thickness direction of a metal sheet in which a main component is composed of a metal, and a connection portion having a positioning hole formed at the periphery of the filtration portion, be provided, and at least one of the cover member and the accommodation member be provided with a protrusion that is inserted into the positioning hole at a position corresponding to the positioning hole when the cancer cell-trapping metal filter member is mounted. According to this configuration, when constituting the cancer cell-trapping device by using the cancer cell-trapping metal filter member, it is possible to perform attachment in a convenient and accurate manner.

In addition, it is preferable that the cover member and the accommodation member be welded to each other. According to this configuration in which the cover member and the accommodation member are welded to each other, fixing of the inside including the cancer cell-trapping metal filter becomes easy and sealing is reliably performed.

In addition, according to still another aspect of the invention, there is provided a method of manufacturing a cancer cell-trapping metal filter. The method includes a process of laminating a photoresist on metal foil, a process of overlapping a photomask including a wave-shaped light-transmitting portion on the photoresist and exposing the photoresist, a process of removing an uncured portion of the photoresist by development to form photoresist patterns, a process of performing metal plating between the photoresist patterns to form metal plating patterns having a height lower than a height of the photoresist patterns, a process of removing the metal foil by chemical dissolution to obtain a structure including the metal plating patterns and the photoresist patterns, and a process of removing the photoresist patterns from the structure to obtain the metal plating patterns having a through-hole corresponding to the light-transmitting portion.

According to the above-described method, the photoresist patterns having a wave shape are formed on the metal foil, and the metal plating patterns are formed based on the photoresist patterns, and thus it is possible to obtain the cancer cell-trapping metal filter in which the wave-shaped through-hole is formed. Here, the photoresist patterns have the wave shape instead of a linear shape, and thus the photoresist patterns become a more stable structure. Accordingly, in the process of performing the metal plating between the resist patterns, and the like, it is possible to prevent the resist patterns from collapsing or being peeled from the metal foil, and thus it is possible to improve a yield ratio as the cancer cell-trapping metal filter.

Here, as a configuration capable of effectively obtaining the above-described operation, specifically, it is preferable that the metal foil be adhered to a carrier layer, and the method further include a process of peeling the carrier layer after the process of forming the metal plating patterns.

In addition, it is preferable that an opening ratio of an opening be 10% to 50%.

Furthermore, it is preferable that the method further include a process of plating a surface of the metal plating patterns with gold after the process of obtaining the metal plating patterns.

In addition, according to still another aspect of the invention, there is provided a method of manufacturing a cancer cell-trapping metal filter sheet. The method includes a process of laminating a photoresist on metal foil, a process of overlapping a photomask including a plurality of blocks of wave-shaped light-transmitting portions on the photoresist and exposing the photoresist, a process of removing an uncured portion of the photoresist by development to form photoresist patterns, a process of performing metal plating between the photoresist patterns to form metal plating patterns having a height lower than a height of the photoresist patterns, a process of removing the metal foil by chemical dissolution to obtain a structure including the metal plating patterns and the photoresist patterns, and a process of removing the photoresist patterns from the structure to obtain the metal plating patterns having a through-hole corresponding to the light-transmitting portion.

According to the above-described manufacturing methods, the photoresist patterns having the wave shape are formed on the metal foil, and the metal plating patterns are formed based on the photoresist patterns, and thus it is possible to obtain the cancer cell-trapping metal filter sheet in which the wave-shaped through-hole is formed. Here, the photoresist patterns have the wave shape instead of a linear shape, and thus the photoresist patterns become a more stable structure. Accordingly, in the process of performing the metal plating between the resist patterns, and the like, it is possible to prevent the resist patterns from collapsing or being peeled from the metal foil, and thus it is possible to improve a yield ratio as the cancer cell-trapping metal filter sheet.

Here, as a configuration capable of effectively obtaining the above-described operation, specifically, it is preferable that the metal foil be adhered to a carrier layer, and the method further include a process of peeling the carrier layer after the process of forming the metal plating patterns.

In addition, in the process of overlapping the photomask on the photoresist and exposing the photoresist, it is preferable to use a photomask which includes a second light-transmitting portion different from the light-transmitting portion at the periphery of the blocks of the wave-shaped light-transmitting portions.

In addition, it is preferable that an opening ratio of an opening be 10% to 50%.

Furthermore, it is preferable that the method further include a process of plating a surface of the metal plating patterns with gold after the process of obtaining the metal plating patterns.

In addition, according to still another aspect of the invention, there is provided a method of manufacturing a cancer cell-trapping device. The method includes a process of providing the above-described cancer cell-trapping metal filter on a flow path inside a casing between an inlet channel and an outlet channel in such a manner that a hole diameter of the through-hole in a main surface on an upstream side becomes smaller than a hole diameter on a rear surface side with respect to the main surface, the casing including a cover member which is formed from a light-transmitting resin material and which has the inlet channel from which a liquid to be tested is introduced to the inside of the casing, and an accommodation member that includes the outlet channel through which the liquid to be tested is discharged to the outside of the casing.

Here, it is preferable that the cover member and the accommodation member be welded to each other.

Advantageous Effects of Invention

According to the invention, it is possible to provide a cancer cell-trapping metal filter which has a high opening ratio and is produced with high production efficiency, a cancer cell-trapping metal filter sheet, a cancer cell-trapping device using the cancer cell-trapping metal filter, and manufacturing methods therefor.

BRIEF DESCRIPTION OF DRAWINGS

FIGS. 2(A) and 2(B) are schematic plan views illustrating a shape of a connected through-hole 12 in a surface of a metal sheet, in which FIG. 2(A) illustrates a connected through-hole that is formed by connecting ends of two single holes having a rectangular shape at a predetermined angle, and FIG. 2(B) illustrates a connected through-hole that is formed by connecting ends of two single holes having a rectangular shape with rounded corners at a predetermined angle.

DESCRIPTION OF EMBODIMENTS

Figure 1:
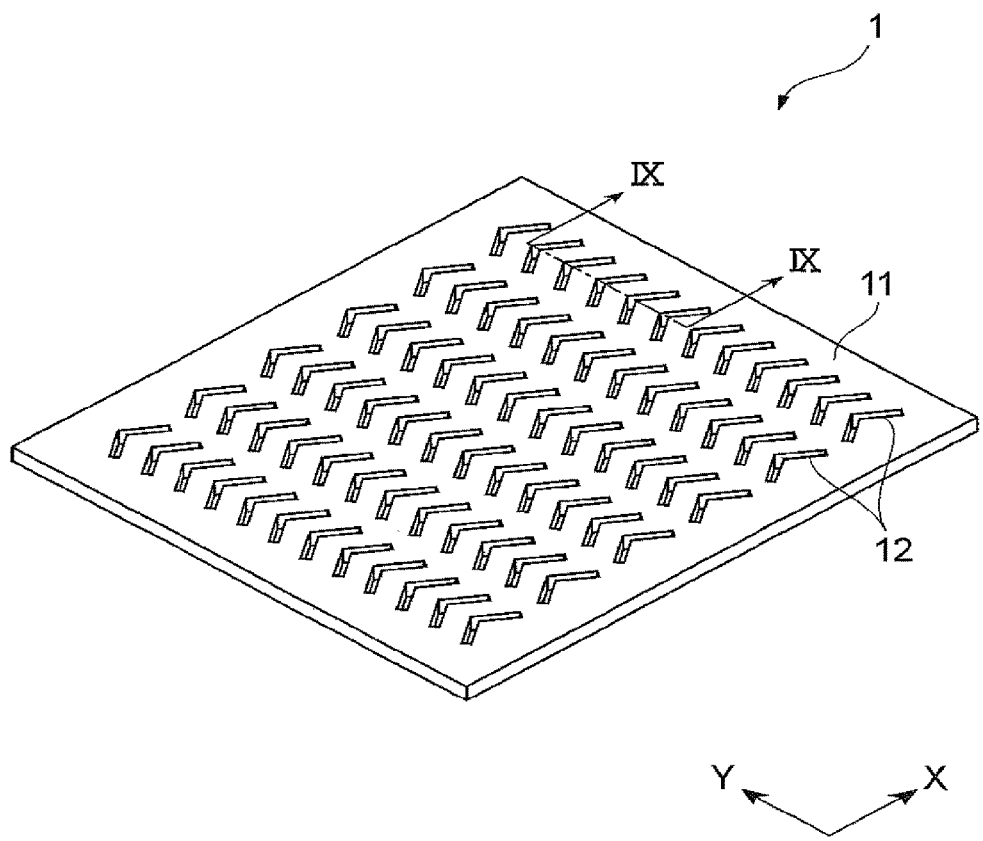
FIG. 1 is a schematic perspective view illustrating a configuration of a cancer cell-trapping metal filter according to this embodiment.

Hereinafter, an embodiment for carrying out the invention will be described in detail with reference to the attached drawings. In addition, in description of the drawings, like reference numerals will be given to the same elements, and a redundant description thereof will be omitted. In addition, the attached drawings are schematic views for easy understanding, and dimensions, dimensional ratios, and the like are different from actual values. In addition, a term "process" in this specification is not intended to represent only an independent process. Even though the process is not clearly distinguished from a different process, when an expected operation of the process is achieved, the different process is also included in the term. In addition, a numerical range illustrated using "to" represents a range including numerical values described before and after "to" as the minimum value and the maximum value, respectively.

(Cancer Cell-Trapping Metal Filter)

FIG. 1 is a schematic perspective view illustrating a configuration of a cancer cell-trapping metal filter according to this embodiment. A cancer cell-trapping metal filter 1 shown in FIG. 1 is a filter which allows red blood cells, blood platelets, and white blood cells (these are collectively referred to as "blood cell components") which are included in blood of a metastatic cancer patient to pass therethrough and which traps a CTC.

As shown in FIG. 1, in the cancer cell-trapping metal filter 1, a plurality of connected through-holes 12 (through-holes) are formed in a metal sheet 11 in a thickness direction, and a shape of the connected through-holes 12 in a surface of the metal sheet 11 is a wave shape. Each of the wave-shaped connected through-holes is formed by connecting ends of a plurality of single holes having a rectangular shape or a rectangular shape with rounded corners on the surface of the metal sheet at a predetermined intersecting angle. In addition, in FIG. 1, XY coordinate axes along a main surface of the cancer cell-trapping metal filter 1 are described for explanation. In the cancer cell-trapping metal filter 1 shown in FIG. 1, the wave shape of the connected through-hole 12 is formed along an X-axial direction.

A metal is a main component of a material of the metal sheet 11 that constitutes the cancer cell-trapping metal filter 1. Here, the main component represents a component, which is included in the highest ratio, among materials that constitute the metal sheet. When the metal is used as the main component of the material that constitute the sheet of the cancer cell-trapping metal filter 1, a variation in hole size is small, and thus separation of the CTS with high separation accuracy and concentration thereof are possible. In addition, the metal is more rigid in comparison to other materials such as plastic, and thus even when a force is applied from the outside, the size or shape of the metal tends to be maintained. Accordingly, even when a blood component (particularly, a white blood cell), which is slightly larger than a hole diameter of the connected through-hole, is deformed and is allowed to pass through the connected through-hole, it is considered that the separation with high accuracy and the concentration are possible. A cell having approximately the same size as the CTC is present in the white blood cell, and thus separation of the CTC with high concentration may be difficult by only using a difference in size. However, since the white blood cell has deformability larger than that of the CTC, the white blood cell can pass through a hole smaller than the size of the white blood cell due to an external force such as suction and compression, and thus it is considered that the white blood cell can be separated from the CTC.

Examples of the material of the metal that is used in the metal sheet 11 include gold, silver, copper, aluminum, tungsten, nickel, chrome, and an alloy of these metals, but there is no limitation thereto. In addition, the metal may be used as an elementary substance, or may be used an ally with other metals or metal oxides so as to apply functionality. From the viewpoints of a price or easy availability, it is preferable to use nickel, copper, gold, and metals including these metals as a main component, and particularly, it is preferable to use a metal including nickel as a main component. In addition, in a case where the metal sheet 11 is formed from a material including nickel as a main component, it is preferable that gold plating be performed on a surface of nickel. Oxidation of a filter surface can be prevented due to the gold plating, and thus adhesiveness of the CTC and the blood cell components with respect to the filter becomes constant. Accordingly, it is possible to raise reproducibility of data.

It is preferable that the thickness of the cancer cell-trapping metal filter 1 be 3 μm to 100 μm. In a case where the film thickness is set in the above-described range, handling of the filter is easy, and the thickness is appropriate for accurate processing.

In addition, it is preferable that the size of the cancer cell-trapping metal filter 1 be 25 mm$^2$ to 1000 mm$^2$, more preferably 25 mm$^2$ to 225 mm$^2$, and still more preferably 25 mm$^2$ to 100 mm$^2$ When the size of the cancer cell-trapping metal filter 1 exceeds 1000 mm$^2$, a dead space increases. In addition, when the size is less than 25 mm$^2$, a processing time is lengthened. In addition, the size of the cancer cell-trapping metal filter 1 has a relation with a configuration of a cancer cell-trapping device on which the cancer cell-trapping metal filter 1 is mounted, and thus details of the size will be described later.

Next, the shape of the connected through-hole 12 that is provided in the cancer cell-trapping metal filter 1 will be described.

Figure 2A:
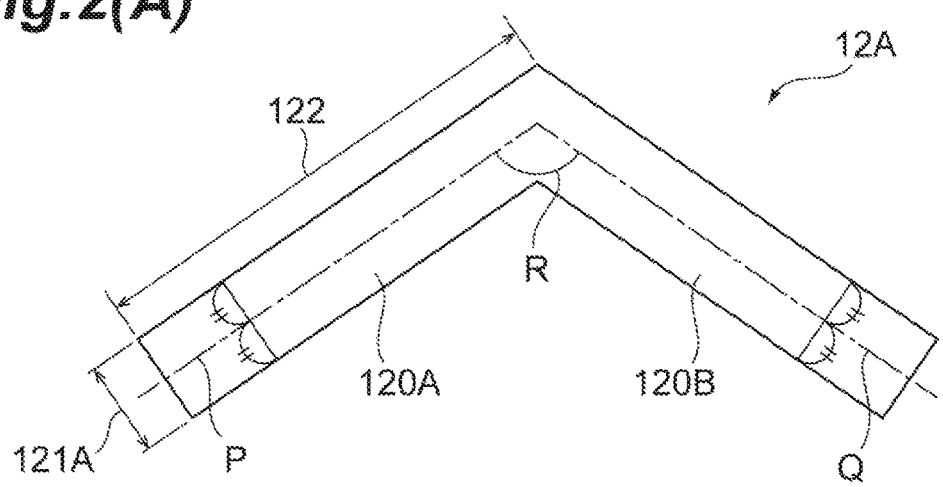
Figure 2B:
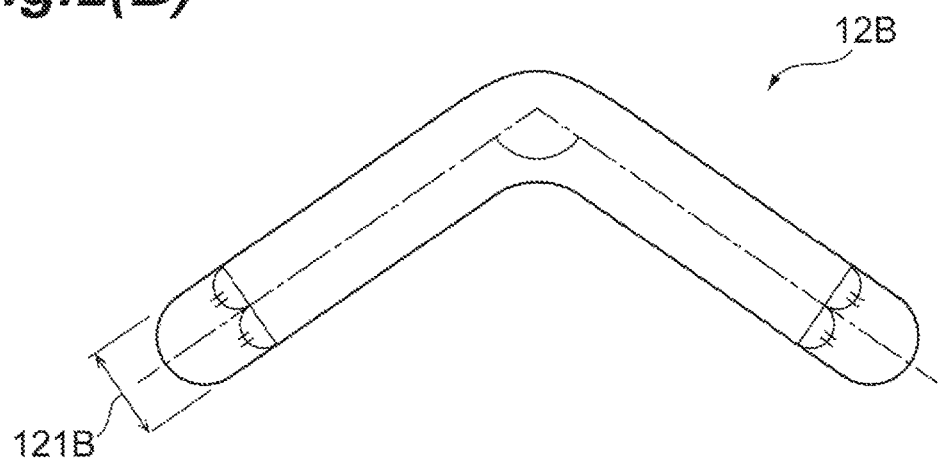

FIGS. 2(A) and 2(B) are schematic plan views illustrating the shape of the connected through-hole 12 in the surface of the metal sheet 11. FIG. 2(A) illustrates a connected through-hole 12A that is formed by connecting ends of two single holes having a rectangular shape at a predetermined angle, and FIG. 2(B) illustrates a connected through-hole 12B that is formed by connecting ends of two single holes having a rectangular shape with rounded corners at a predetermined angle. Here, the rectangular shape with rounded corners represents a rectangular shape whose corners are round, and examples of this shape include a shape having two long sides equal in length and two semicircles, and in which a semicircle centering around a middle point of a short side of a rectangle is respectively provided on an outer side of two short sides of the rectangle.

In addition, in the size of the connected through-hole 12 having the rectangular shape or the rectangular shape with rounded corners (hereinafter, these shapes are collectively referred to as "approximately rectangular shape"), a length range of each short side (indicated by a short side 121A in FIG. 2(A) and a short side 121B in FIG. 2(B)) is approximately 5.0 μm to 15.0 μm. On the other hand, the length of each long side (indicated by a long side 122 in FIG. 2(A)) of the connected through-hole 12 can be appropriately changed in a range in which the connected through-holes 12 (12A and 12B) do not intersect an outer frame of the cancer cell-trapping metal filter 1, and the range is approximately 10 μm to 5 mm.

In addition, a hole diameter of the cancer cell-trapping metal filter 1 is changed in response to the size of the CTC that is an object to be trapped. Here, the hole diameter of the connected through-hole is defined as the maximum value of a diameter of a ball which is capable of passing through each connected through-hole in a non-deformed state. For example, the hole diameter of the connected through-holes 12A and 12B becomes the length 121A or 121B of the short side of the connected through-holes. In a case where the shape of the hole is a rectangular shape or a rectangular shape with rounded corners, even in a state in which a component that is an object to be trapped is trapped, a gap can be formed in a long-side direction of the hole. A liquid can pass through the gap, and thus flogging of the filter can be prevented.

In the connected through-hole 12 of the cancer cell-trapping metal filter 1, the wave shape is formed by connecting ends of the two single holes 120A and 120B, and thus an excessive space between the single holes 120A and 120B can be saved. Accordingly, a plurality of the single holes can be disposed to be closer to each other, and thus it is possible to improve an opening ratio that is represented by an area of the through-holes (single holes or connected through-holes) per unit area in the filter surface.

It is preferable that the plurality of connected through-holes 12 be disposed to be close to each other in the same direction. In the cancer cell-trapping metal filter 1 of FIG. 1, each of the connected through-holes 2 is formed by connecting an one end of each of two single holes having an approximately rectangular shape, and thus an arrangement direction of the connected through-holes 12 in the filter surface can be aligned in such a manner that the centers of the connected through-holes 12 which become connection portions are arranged to be closer to each other. According to this, the opening ratio of the cancer cell-trapping metal filter 1 is improved, and thus it is possible to separate and concentrate the CTC in blood with efficiency. In addition, when the connected through-holes 12 are arranged to be close to each other as described above, it is possible to make an area of a filtration portion in the cancer cell-trapping metal filter 1 small. Here, the filtration portion represents a region that functions as a filter in the entirety of the cancer cell-trapping metal filter 1, that is, a region in which the connected through-holes 12 are formed. In a case where the area of the connected through-hole 12 formed in the cancer cell-trapping metal filter 1 is same in each case, when the connected through-hole 12 are densely arranged by making the connected through-hole 12 close to each other, the area of the filtration portion can be made small, and separation efficiency of the CTC in the region can be raised. The area of the filtration portion will be described later.

In addition, it is not necessary to limit the shape of the plurality of connected through-holes 12, which are formed in the same cancer cell-trapping metal filter 1, to one kind, and the shape can be appropriately changed. However, as shown in FIG. 1, when the shape is set to the wave shape, it is possible to raise a ratio of the connected through-holes 12 with respect to the area of the filtration portion of the cancer cell-trapping metal filter 1.

In the cancer cell-trapping metal filter 1 according to this embodiment, as shown in FIG. 2(A), in a case of connecting ends of the two single holes 120A and 120B having an approximately rectangular shape, a corner having an angle of less than 180° in corners, which are formed at an intersection between central axial lines of the two single holes 120A and 120B, is referred to as an intersection angle R. In addition, in a case where a plurality of the wave-shaped connected through-holes 12 formed by connecting ends of two single holes having an approximately rectangular shape are formed in the cancer cell-trapping metal filter 1, it is preferable that the intersection angle R in each of the connected through-holes 12 be approximately the same as that in other connected through-holes 12. This is because in a case where the intersection angle R of the plurality of connected through-holes 12 is common in each case, it is possible to reduce an area of a region in which the connected through-hole 12 is not formed when the connected through-holes 12 are disposed to be close to each other.

In addition, the intersection angle R in the connected through-hole 12 may be measured by using a scanning electron microscope. Specifically, as shown in FIG. 2(A), in angles made by a central line P and a central line Q at an intersection between the central line P of the single hole 120A having an approximately rectangular shape in a long-side direction and the central line Q of the single hole 120B having an approximately rectangular shape in the long-side direction, an angle of less than 180° becomes the intersection angle R. In addition, it is preferable that the intersection angle R between the two single holes 120A and 120B which have an approximately rectangular shape be 30° to 150° in consideration of forming easiness of the connected through-hole 12, more preferably 45° to 135°, and still more preferably 60° to 120°.

In the cancer cell-trapping metal filter 1, in a case of arranging the plurality of connected through-holes 12, it is preferable that a spatial distance in a Y-direction between the connected through-holes 12 that are adjacent to each other be 10 μm to 115 μm, more preferably 15 μm to 65 μm, and still more preferably 20 μm to 45 μm. When the spatial distance is less than 10 μm, there is a tendency that arrangement and formation of the connected through-holes 12 become difficult. When the spatial distance exceeds 115 μm, the opening ratio decreases, and thus there is a tendency that remaining of a blood cell component that is a noise increases. In addition, it is preferable that a spatial distance in an X-direction be 10 μm to 300, more preferably 30 μm to 200 μm, and still more preferably 35 μm to 100. When the spatial distance in the X-direction is less than 10 μm, there is a tendency that the arrangement and formation of the connected through-holes 12 become difficult. When the spatial distance exceeds 300 μm, the opening ratio decreases, and thus there is a tendency that remaining of a blood cell component that is a noise increases.

Figure 13:
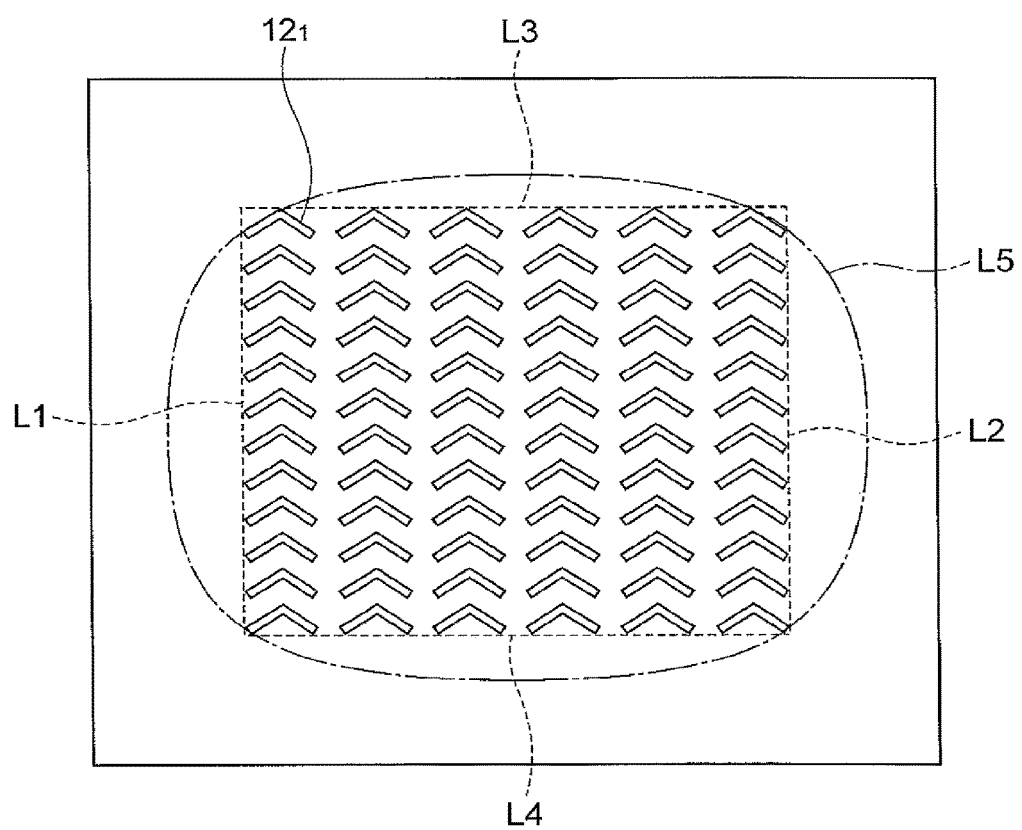
FIG. 13 is a view illustrating a method of calculating an area of a region having a filter function in the cancer cell-trapping metal filter.

In addition, it is preferable that the opening ratio of the connected through-holes in the cancer cell-trapping metal filter 1 be 10% to 50%, more preferably 10% to 40%, and still more preferably 10% to 30%. The opening ratio represents a ratio of an area occupied by the through-holes (single holes or connected through-holes) to an area of a region functioning as a filter in the cancer cell-trapping metal filter 1 (refer to FIG. 13). Here, the area of the region functioning as a filter is an area of a rectangular or elliptical region shown in FIG. 13. That is, the area of the region functioning as a filter is an area of a rectangle formed by two straight lines L1 and L2 which are obtained by connecting ends of the connected through-holes along an arrangement direction (the Y-direction of the cancer cell-trapping metal filter 1) of the connected through-holes among the plurality of connected through-holes included in the cancer cell-trapping metal filter, a straight line L3 which is perpendicular to the two straight lines and which is obtained by connecting the central connection portions of the connected through-holes along the X-direction of the cancer cell-trapping metal filter 1, and a straight line L4 which is obtained by connecting ends of the connected through-holes along the X-direction of the cancer cell-trapping metal filter 1, or an area of the smallest ellipse L5 among ellipses that are formed to come into contact with connected through-holes and include all of the connected through-holes.

In addition, when calculating the area of the region functioning as a filter, the smallest area in the rectangle and the ellipse is employed as the area of the region functioning as a filter. For example, in a case of the filter shown in FIG. 13, since the area of the rectangle obtained by connecting L1 to L4 is smaller than the area of the ellipse L5 that is formed to come into contact with connected through-holes and include all of the connected through-holes, the area of the rectangle is employed as the area of the region functioning as a filter. In addition, as described later, in the cancer cell-trapping metal filter, a length of a short side of each connected through-hole on one surface side is larger than a length of a short side of the connected through-hole on the other surface side. In this case, when calculating or measuring the opening ratio, the small length of the short side of the connected through-holes is employed. In addition, it is preferable that a difference between the length of the short side of the connected through-hole 12 on one surface side and the length of the short side of the connected through-hole 12 on the other surface side be 0.1 μm to 2.5 μm, more preferably 0.1 μm to 2.0 μm, and still more preferably 0.1 μm to 1.5 μm.

The opening ratio can be obtained by calculation on the basis of the above-described definition in some cases. In addition, the opening ratio may be set as follows. Specifically, a mask film having an opening corresponding to the area of the region functioning as a filter is provided between a light-emitting unit and a light-receiving unit of a spectrophotometer, and an average value of absorbance of visible rays of 400 nm to 800 nm is obtained. Then, the cancer cell-trapping metal filter is provided between the light-emitting unit and the light-receiving unit of the spectrometer, and an average value of absorbance of visible rays of 400 nm to 800 nm is obtained. A ratio (%) of the absorbance of the cancer cell-trapping metal filter to the absorbance of the area of the region functioning as a filter is set as the opening ratio. In addition, the area of the light-emitting unit of the spectrophotometer may be smaller than the area of the region functioning as a filter. In this case, measurement is performed three times by arbitrarily changing a measurement region in the region functioning as a filter, and then an average value of the opening ratio is set as the opening ratio of the filter. At this time, measurement regions may be partially overlapped each other. The larger the opening ratio is, the more preferable from the viewpoint of prevention of clogging. However, when the opening ratio exceeds 50%, there is a possibility that a decrease in strength of the filter, a decrease in yield ratio due to difficulty in processing, and the like may occur. In addition, when the opening ration is less than 10%, clogging tends to occur, and thus a concentration performance of the filter may deteriorate.

In addition, a shape of the through-hole that is provided to the cancer cell-trapping metal filter is not limited to the shape shown in FIG. 1 as long as the shape is a wave shape. FIG. 3, FIG. 4, FIG. 15, and FIG. 16 illustrate examples of the cancer cell-trapping metal filter 1 in which the shape of the through-hole is different in each case. In a cancer cell-trapping metal filter 1A shown in FIG. 3, a wave-shaped connected through-hole 13, which is obtained by connecting ends of three single holes in such a manner that single holes having a rectangular shape extend in the X-axis direction of the cancer cell-trapping metal filter 1A, is provided. As shown in the cancer cell-trapping metal filter 1A, in a case of connecting the three single holes having a rectangular shape, it is preferable to obtain the wave shape by connecting the single holes having a rectangular shape in such a manner that directions of an intersection angle in adjacent connection portions are opposite to each other in order for the connected through-hole 13 to have an S-shape as a whole. The intersection angle may be continuously formed on the same side with respect to the central axial line of a rectangle, but formation of the intersection angle may be appropriately changed in accordance with a yield ratio during manufacturing of the cancer cell-trapping metal filter, accuracy in size of the connected through-hole, the opening ratio of the filter as a whole, and the like.

Figure 4:
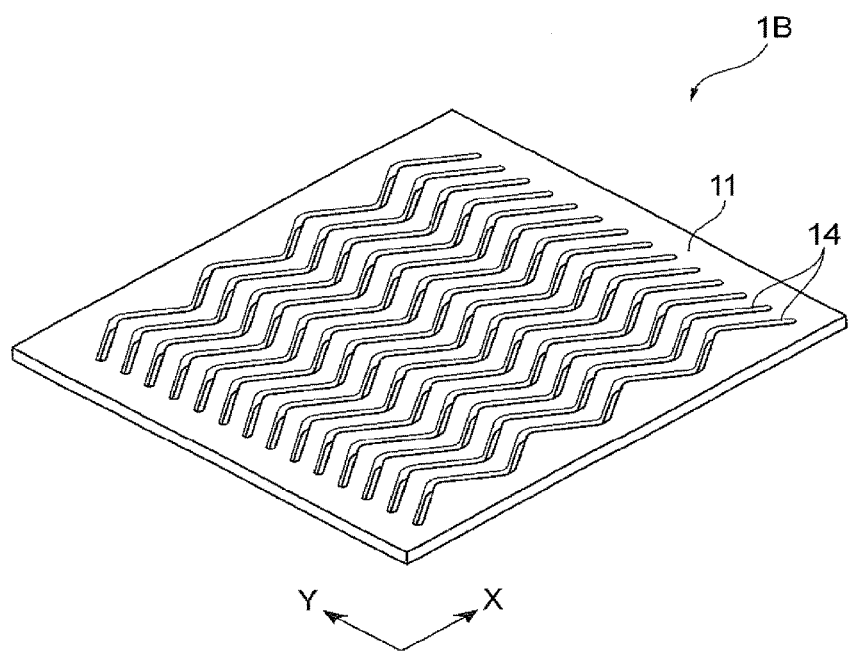
FIG. 4 is a schematic perspective view illustrating an example the cancer cell-trapping metal filter in which the shape of the connected through-hole is different.

In addition, in a cancer cell-trapping metal filter 1B shown in FIG. 4, a wave-shaped connected through-hole 14, which is obtained by connecting ends of eight shingle holes having a rectangular shape with rounded corners while changing an angle along the X-axial direction, is provided. In this case, it is also preferable to obtain the wave shape by connecting the single holes having a rectangular shape with rounded corners in such a manner that directions of an intersection angle in adjacent connection portions of the single holes having a rectangular shape with rounded corners are opposite to each other. In addition, in FIG. 4, only one row is arranged along the Y-axial direction of the cancer cell-trapping metal filter 1B due to a page space, but a plurality of rows may be arranged.

Figure 15:
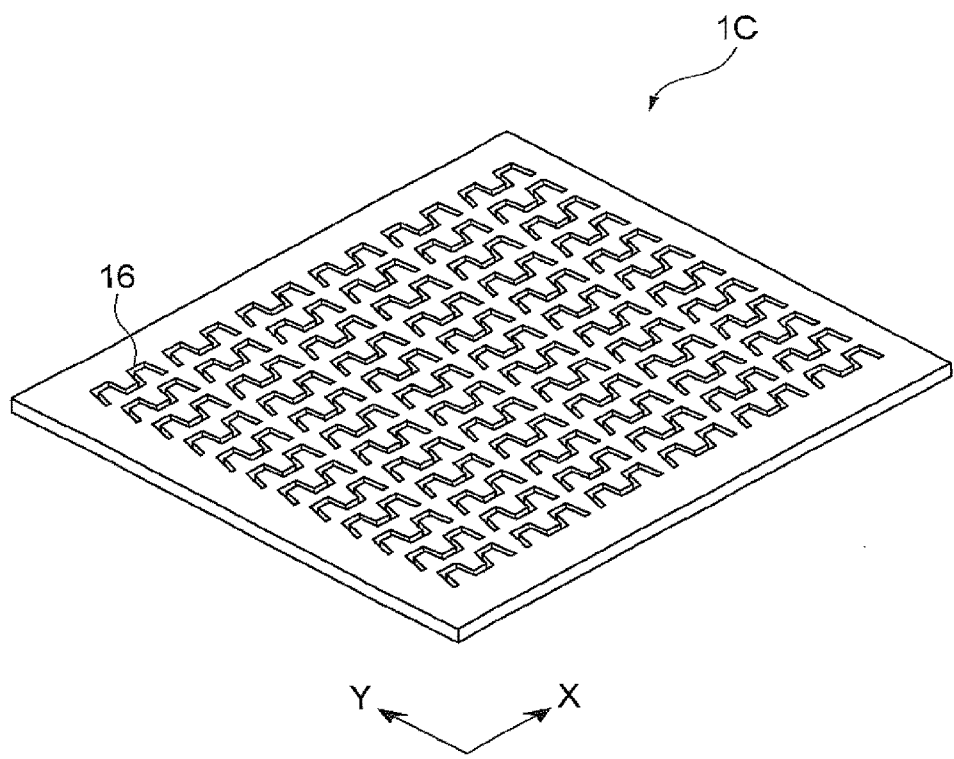
FIG. 15 is a schematic perspective view illustrating an example of the cancer cell-trapping metal filter in which a shape of the connected through-hole is different.

In addition, in a cancer cell-trapping metal filter 1C shown in FIG. 15, a wave-shaped connected through-hole 16, which is obtained by connecting ends of seven single holes having a rectangular shape with rounded corners while changing an angle along the X-axial direction, is provided. In a case of the connected through-hole 16, a wave shape in which a single hole extending in the X-axial direction and a single hole extending in a direction intersecting the X-axis are alternately connected, and the single hole extending in the X-axial direction forms the bottom of a wave.

Figure 16:
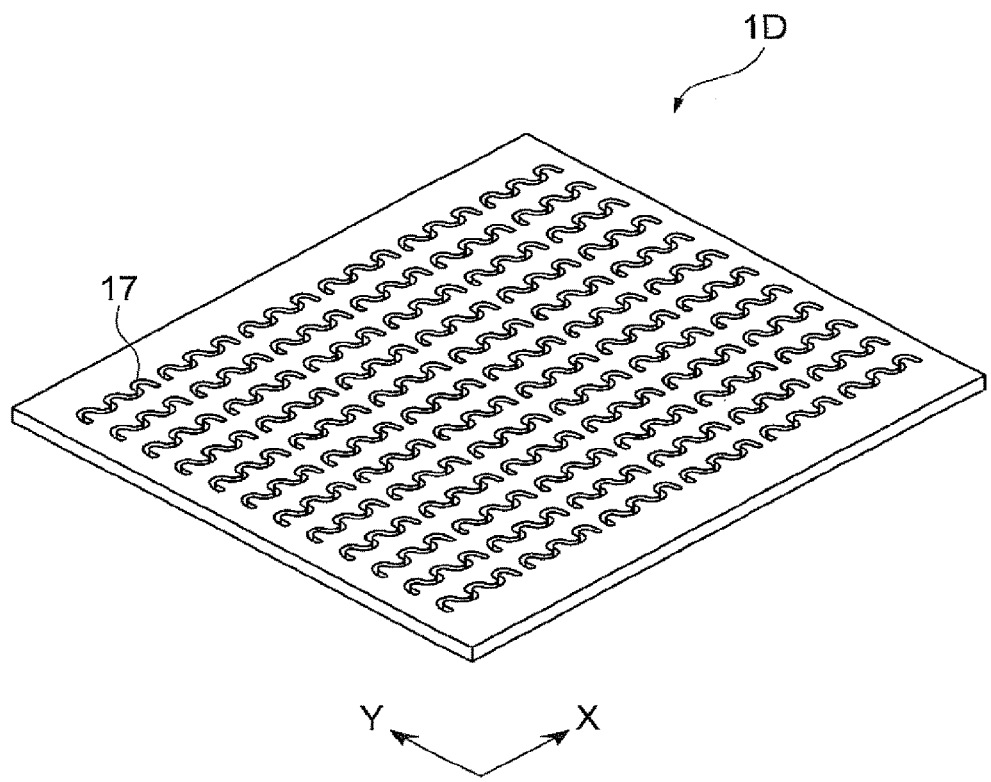
FIG. 16 is a schematic perspective view illustrating an example of the cancer cell-trapping metal filter in which a shape of the connected through-hole is different.

In addition, in a cancer cell-trapping metal filter 1D shown in FIG. 16, a wave-shaped through-hole 17, which is obtained by connecting ends in such a manner that semicircles are alternately opposite to each other and which extends in the X-axial direction, is provided. The through-hole 17 is preferable when considering that the through-hole is formed with one curved line differently from other cancer cell-trapping metal filters, and thus a length of a short side of the through-hole can be designed to be approximately constant. For example, the through-hole 17 can be formed by drawing photoresist patterns using a CAD. It is not necessary for the through-hole provided in the cancer cell-trapping metal filter to be a connected through-hole obtained by connecting ends of a plurality of single holes, in which a shape in a surface of a metal sheet is a rectangular shape or a rectangular shape with rounded corners, with a predetermined intersection angle. Similar to the through-hole 17 in the cancer cell-trapping metal filter 1D, an external shape in the surface of the metal sheet may be formed with a curved line.

Figure 3:
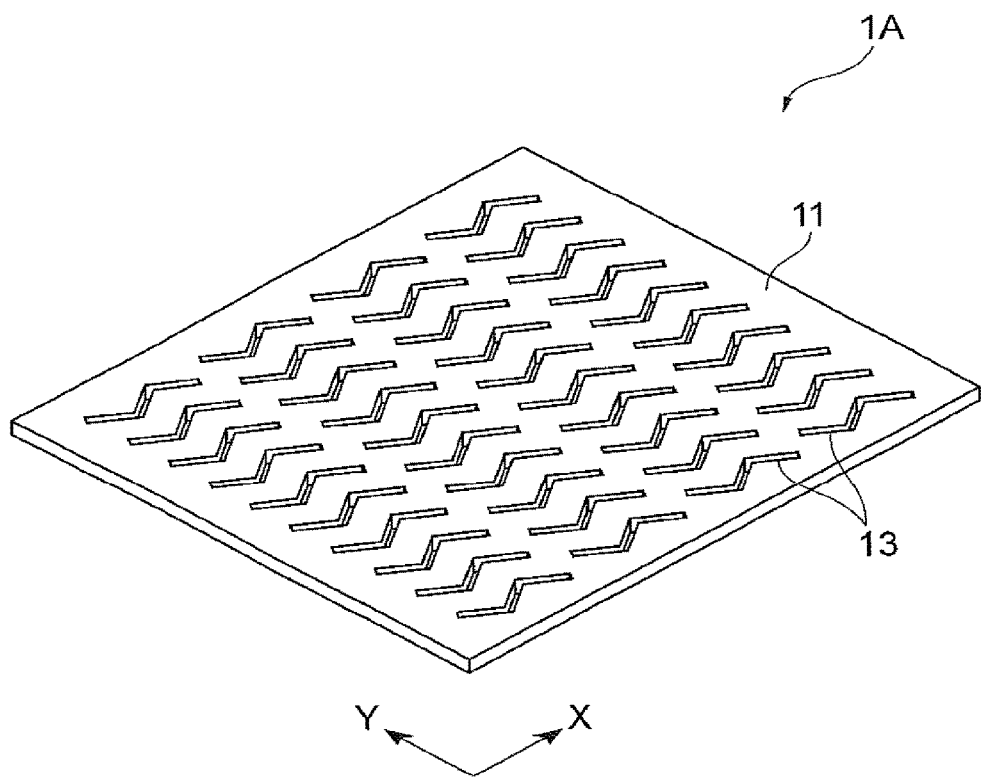
FIG. 3 is a schematic perspective view illustrating an example of the cancer cell-trapping metal filter in which a shape of the connected through-hole is different.

In any of the cancer cell-trapping metal filter 1A shown in FIG. 3 and the cancer cell-trapping metal filter 1B shown in FIG. 4, connected through-holes having a wave shape can be disposed adjacent to each other, and thus the opening ratio in the cancer cell-trapping metal filter is improved. In addition, each of the connected through-hole is set to have a wave shape, and thus a yield ratio in the following manufacturing process can be improved. Details of this will be described later.

(Cancer Cell-Trapping Metal Filter Sheet)

Figure 5:
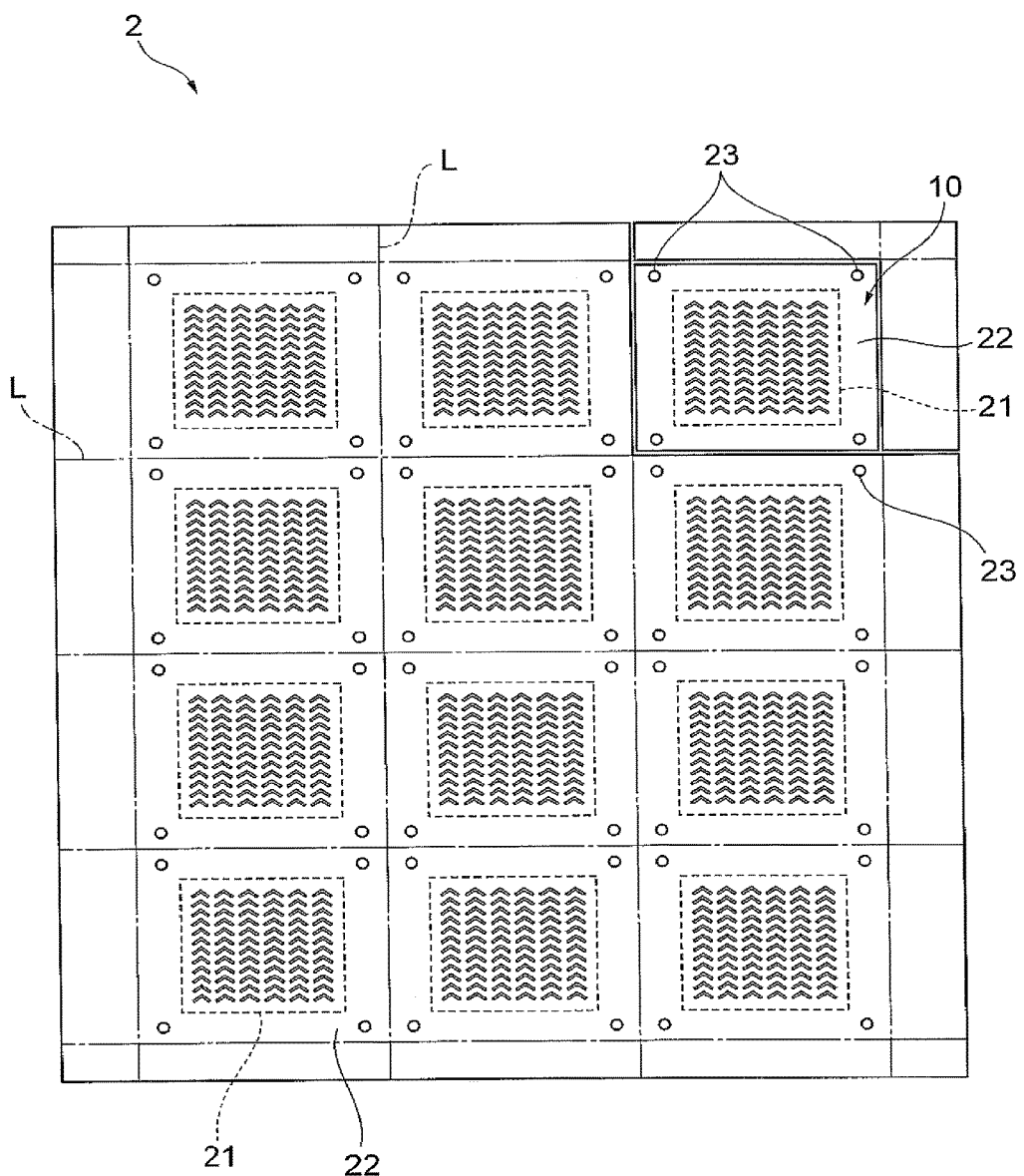
FIG. 5 is a schematic top view illustrating a configuration of a cancer cell-trapping metal filter sheet according to this embodiment.

Next, a cancer cell-trapping metal filter sheet 2 according to this embodiment will be described. FIG. 5 is a schematic top view illustrating a configuration of the cancer cell-trapping metal filter sheet 2 according to this embodiment. The cancer cell-trapping metal filter sheet 2 is a sheet to efficiently produce a plurality of the cancer cell-trapping metal filters, and cancer cell-trapping metal filter members 10, which are obtained by performing cutting along a cutting line L as shown in FIG. 5, can be respectively used as the cancer cell-trapping metal filter. An individual piece after the cutting, that is, each of the cancer cell-trapping metal filter member 10 includes a filtration portion 21 in which the plurality of connected through-holes 12 are formed, and a connection portion 22 that is provided at the periphery of the filtration portion 21. Among the components, the filtration portion 21 has the same function as the cancer cell-trapping metal filter 1.

The cancer cell-trapping metal filter sheet 2 before the cutting includes the filtration portion 21 in which the plurality of connected through-holes 12 are formed and a main component is composed of a metal, and the connection portion 22 which is formed from the same material as the filtration portion 21 and which connects between adjacent filtration portions 21.

In addition, it is preferable that a positioning hole 23 different from the wave-shaped connected through-holes in the filtration portion 21 be formed in the connection portion 22 provided on an outer side of each filtration portion 21 of the cancer cell-trapping metal filter sheet. The positioning hole 23 is used to mount the filtration portion 21, which is obtained by the cutting along the cutting line L, at a predetermined position of the following cover member or accommodation member.

It is preferable that the filtration portion 21 have the opening ratio of the connected through-holes 12 be 10% to 50%, more preferably 10% to 40%, and still more preferably 10% to 30%. The opening ratio represents a ratio of an area occupied by the through-holes (single holes or connected through-holes) to an area of a region functioning as a filter, and can be calculated by measurement using a spectrophotometer. The larger the opening ratio is, the more preferable from the viewpoint of prevention of clogging. However, when the opening ratio exceeds 50%, the strength of the filtration portion 21 may decrease or processing may be difficult. In addition, when the opening ratio is less than 10%, the clogging tends to occur, and thus a performance as a filter may deteriorate.

Similar to the metal sheet 11 of the cancer cell-trapping metal filter 1, in the cancer cell-trapping metal filter sheet 2, a main component is composed of a metal. Examples of a material of the metal include gold, silver, copper, aluminum, tungsten, nickel, chrome, and alloys of these metals, but there is no limitation thereto. In addition, it is preferable that gold plating be performed on a surface of the cancer cell-trapping metal filter sheet 2. Oxidation of a filter surface can be prevented due to the gold plating, and thus adhesiveness of the CTC and the blood cell components with respect to the filter becomes constant. Accordingly, it is possible to raise reproducibility of data.

(Cancer Cell-Trapping Device)

Figure 6:
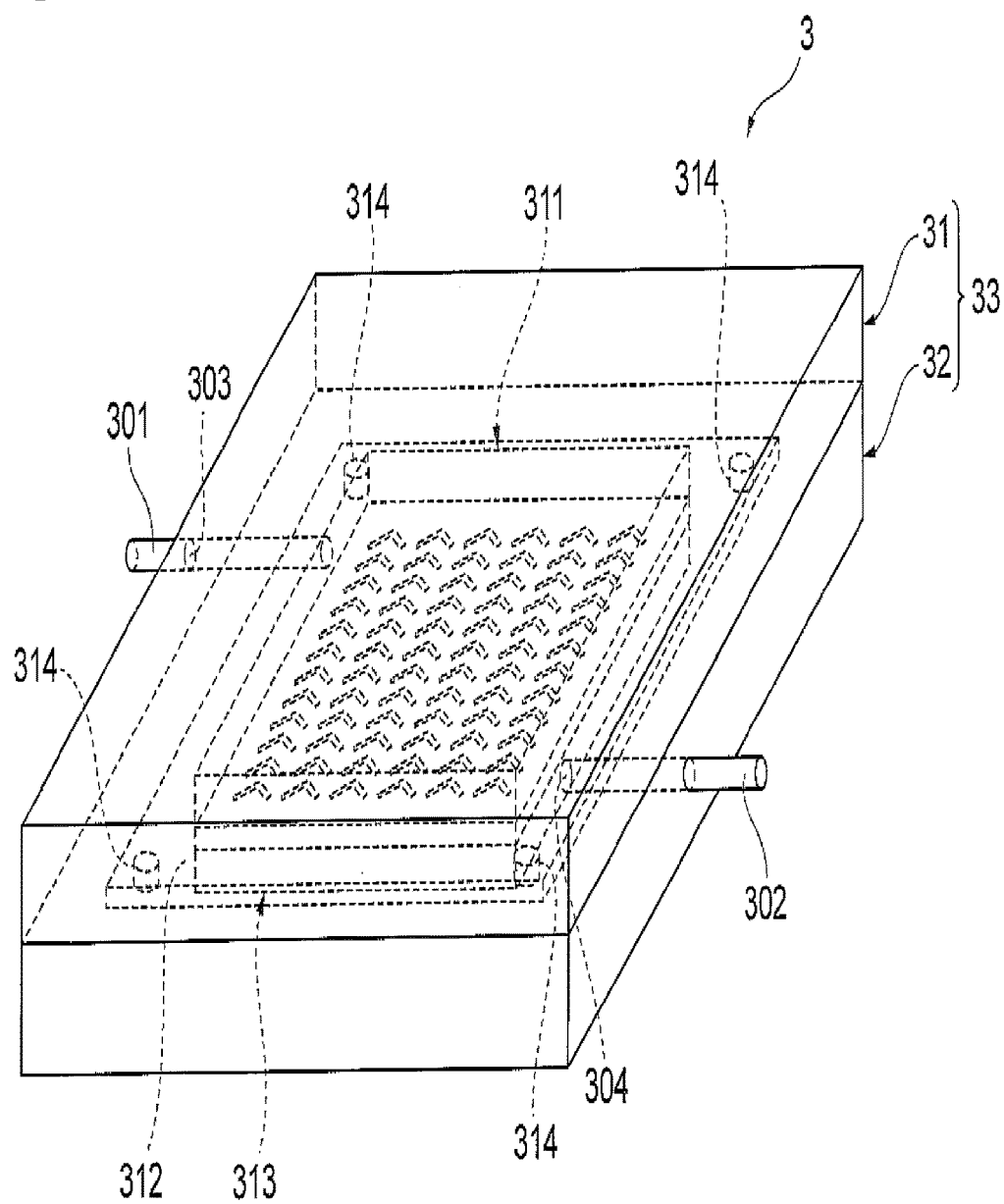
FIG. 6 is a schematic perspective view of a cancer cell-trapping device according to this embodiment.
Figure 7:
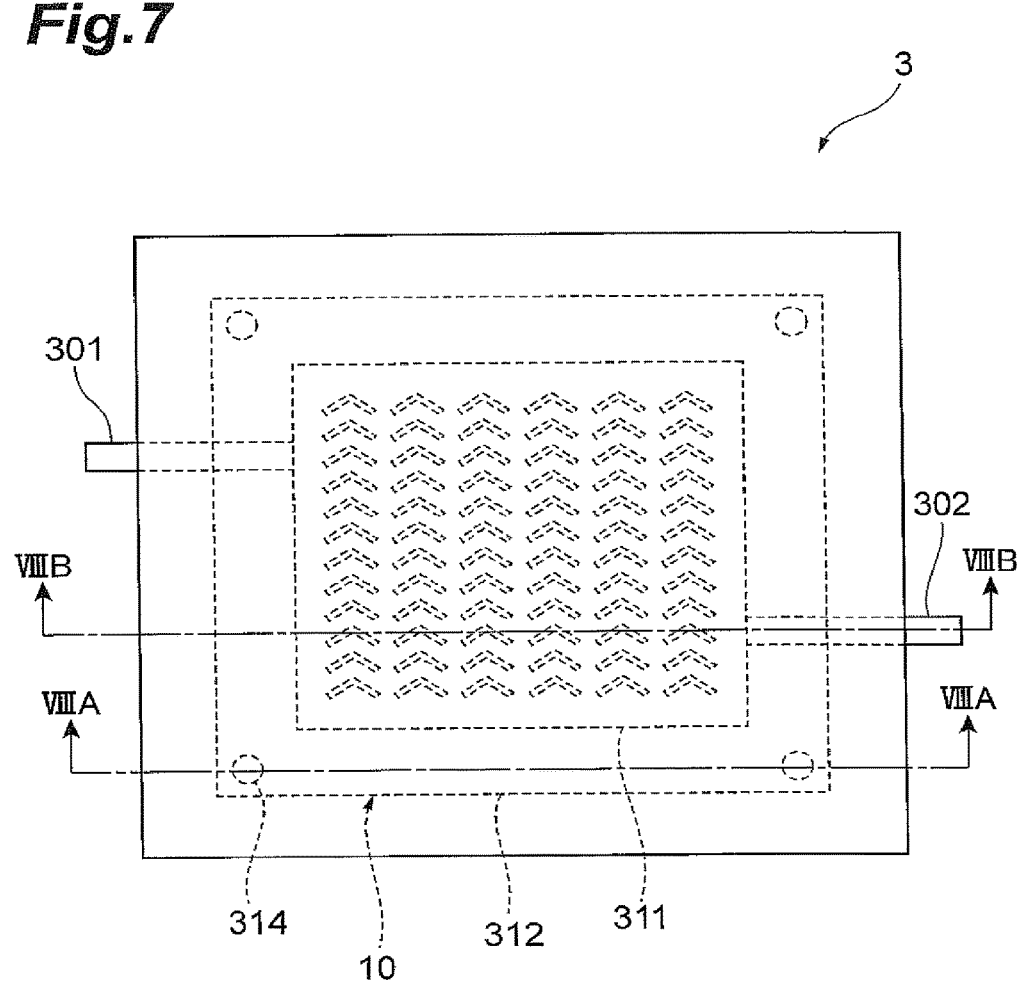
FIG. 7 is a schematic plan view of the cancer cell-trapping device shown in FIG. 6.
Figure 8A:
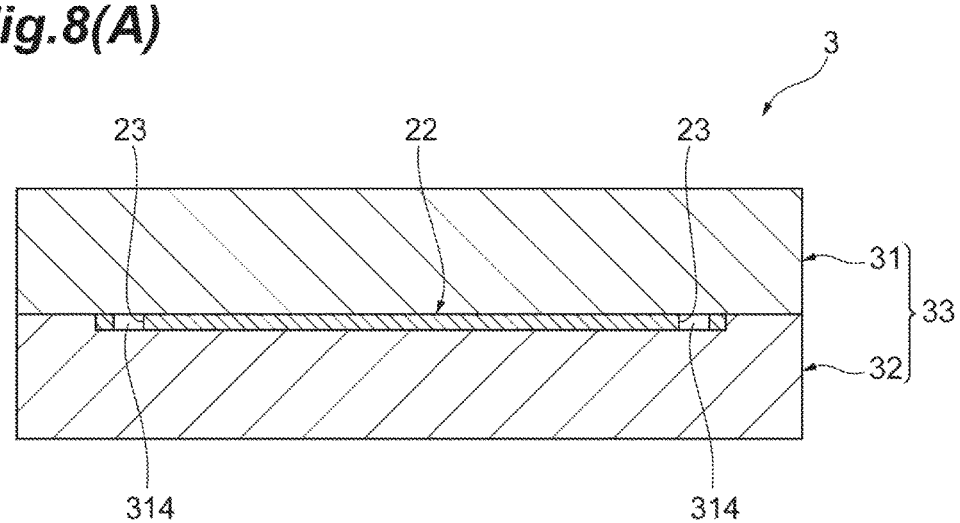
FIG. 8(A) is a cross-sectional view taken along line VIIIA-VIIIA in FIG. 7.
Figure 8B:
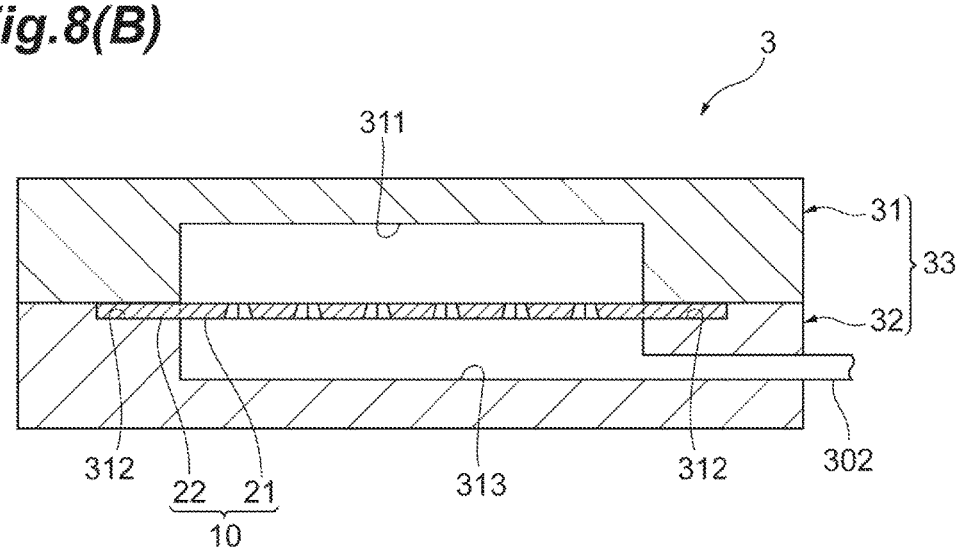
FIG. 8(B) is a cross-sectional view taken along line VIIIB-VIIIB in FIG. 7.

Next, a description will be given to a configuration of a cancer cell-trapping device 3 in which the cancer cell-trapping metal filter 1 according to this embodiment is mounted and is used. FIG. 6 is a schematic perspective view of the cancer cell-trapping device 3. In addition, FIG. 7 is a schematic plan view of the cancer cell-trapping device 3. In addition, FIG. 8(A) is a cross-sectional view taken along line VIIIA-VIIIA in FIG. 7, and FIG. 8(B) is a cross-sectional view taken along line VIIIB-VIIIB in FIG. 7.

The cancer cell-trapping device 3 according to this embodiment includes a casing 33 that is formed from a transparent resin, and the cancer cell-trapping metal filter 1 through which a cell-dispersed liquid that is a liquid to be tested passes. In addition, the casing 33 is configured to include a cover member 31 having an inlet channel 301 from which a CTC-including liquid to be tested is introduced to the inside of the casing, and an accommodation member 32 that has an outlet channel 302 through which the liquid to be tested is discharged from the inside to the outside of the casing. The cancer cell-trapping metal filter member 10 is provided between the cover member 31 and the accommodation member 32. In the cancer cell-trapping device 3, the cover member 31 and the accommodation member 32 which have a recessed portion are combined, and thus a space through which the liquid to be tested flows is formed inside the casing 33. The liquid to be tested is introduced through the inlet channel 301 that is connected to the space inside the casing 33, and the liquid to be tested is discharged from the outlet channel 302 that is similarly connected to the space. According to this configuration, a flow path of the liquid to be tested from the inlet channel 301 to the outlet channel 302 is formed. Cancer cell-trapping metal filter is disposed on the flow path of the liquid to be tested, and thus when the liquid to be tested passes through the cancer cell-trapping metal filter, the CTC that is an object to be trapped is trapped by the filter.

Figure 17:
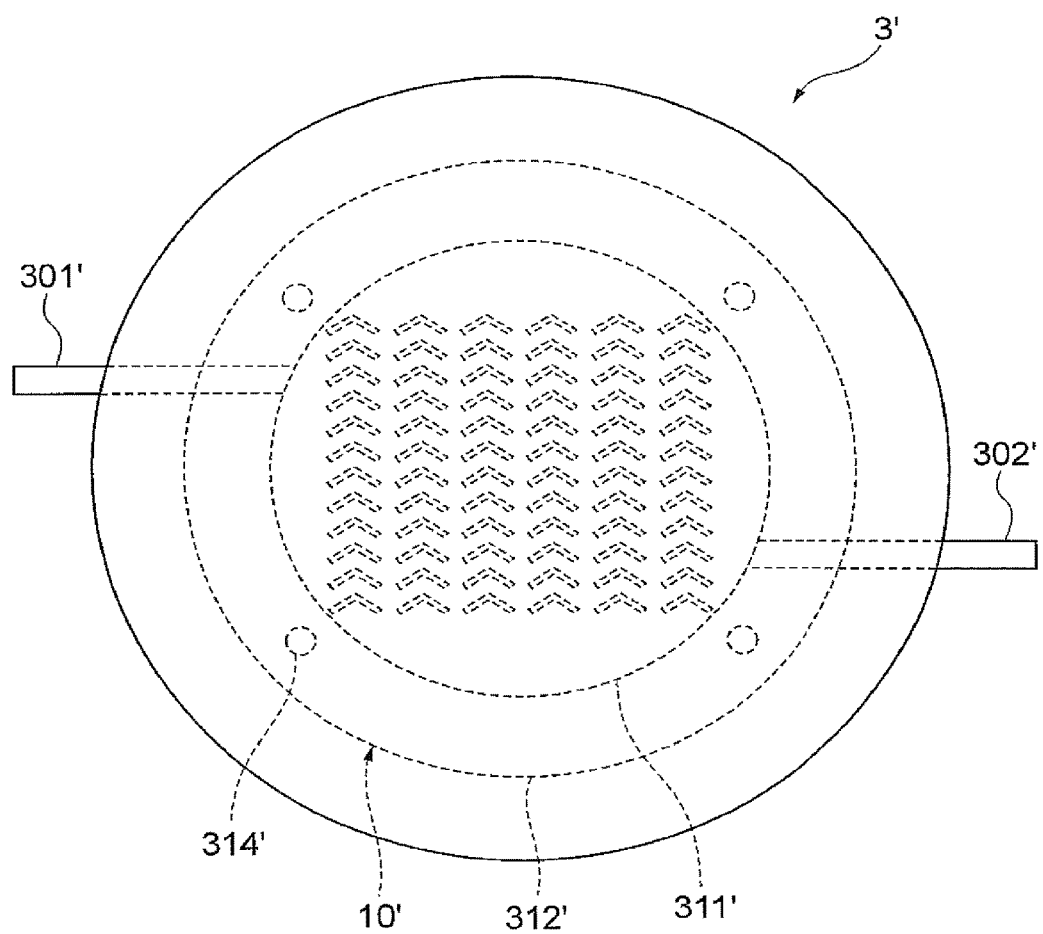
FIG. 17 is a schematic plan view illustrating another configuration of the cancer cell-trapping device.

In addition, the cancer cell-trapping device according to this embodiment may be configured to have other shapes. For example, in a cancer cell-trapping device 3' shown in FIG. 17, a shape of a space through which the liquid to be tested flows is changed from a rectangular shape to an elliptical shape (or a circular shape) in comparison to the cancer cell-trapping device 3. That is, the cancer cell-trapping device 3' includes a casing 33' in which the shape of an upper surface and a lower surface is set to an elliptical shape, and a cancer cell-trapping metal filter 1' through which the cell-dispersed liquid that is the liquid to be tested flows. Furthermore, the casing 33' is configured to include a cover member 31' having an inlet channel 301' and an accommodation member 32' having a discharge flow path 302'. A cancer cell-trapping metal filter member 10' is provided between the cover member 31' and the accommodation member 32'. As described above, the shape of the cancer cell-trapping device may be appropriately changed, and thus the shape of the region functioning as a filter in the cancer cell-trapping metal filter 1' is changed in response to the shape of the inner space.

In addition, in the following embodiment, a description will be given to a configuration of mounting the cancer cell-trapping metal filter member 10, which can be obtained by cutting the cancer cell-trapping metal filter sheet 2 shown in FIG. 5 and which is configured to include the filtration portion 21 and the connection portion 22, on a device.

It is preferable the casing 33 of the cancer cell-trapping device 3 when viewed from an upper side have a size of 5 mm×5 mm to 50 mm×50 mm. In addition, it is preferable that the thickness of the casing be 5 mm to 30 mm. In addition, it is preferable that a material of the casing 33 be substantially transparent in a visible ray range for detection of the CTC. According to this configuration, after allowing blood to flow through the casing to perform a CTC separation and concentration process, it is possible to observe the CTC that is trapped on the cancer cell-trapping metal filter member 10 from the outside without disassembling the device. Specifically, examples of the material of the casing 33 include polymers such as an acrylic resin and polydimethylsiloxane. Among these, the acrylic resin, in which self-fluorescence emitted by the material itself is low when being irradiated with light in a wavelength range of 300 nm to 800 nm during CTC observation, is more preferable, and polymethyl methacrylate is particularly preferable. In a case where the casing 33 is formed from the above-described resins, it is preferable that the casing 33 be produced by injection molding from the viewpoint of production efficiency. In addition, the inlet channel 301 and the outlet channel 302 are demanded to be formed from a transparent resin to confirm passage of the liquid to be tested. However, observation of the CTC is not demanded, and thus the inlet channel 301 and the outlet channel 302 may be formed from a resin different from that of the cover member or the accommodation member.

In addition, in a case where the casing 33 is constituted by a light-transmitting member, it is not necessary to take out the cancer cell-trapping metal filter (in this embodiment, the cancer cell-trapping metal filter member 10) through which the liquid to be tested passes through from the cancer cell-trapping device 3, and thus it is possible to prevent erroneous determination due to adhesion of contaminant to the cancer cell-trapping metal filter, and the like. In addition, it is not necessary to expose the inside of the device, to which a human-derived liquid to be tested or the CTC adheres and which may be contaminated by various pathogens or bacteria, to the outside, and thus it is possible to reduce complication in securement of working stability.

The casing 33 is formed by fixing the cover member 31 and the accommodation member 32 to each other. A shape of the casing 33 is not particularly limited. However, for observation of a material that remains on a surface of the cancer cell-trapping metal filter from the outside after allowing the liquid to be tested to pass through the connected through-holes 12 of the cancer cell-trapping metal filter (in this embodiment, the cancer cell-trapping metal filter member 10) that is accommodated inside the casing 33, it is preferable that upper and lower surfaces that face a main surface of the cancer cell-trapping metal filter be flat and be parallel with each other.

In the casing 33, the cover member 31 includes the inlet channel 301 and an inlet port 303. The inlet channel 301 is disposed at a side surface of the cover member 31. In addition, an introduction region 311, which introduces the liquid to be tested to flow through the cancer cell-trapping metal filter (in this embodiment, the cancer cell-trapping metal filter member 10), is provided in the cover member 31. When the cancer cell-trapping device 3 is viewed from an upper side, the introduction region 311 is provided on an upper side of the filtration portion 21 of the cancer cell-trapping metal filter member 10 to include the entirety of the filtration portion 21 provided with the connected through-holes 12 in the cancer cell-trapping metal filter member 10 that is mounted on the accommodation member 32. The introduction region 311 is connected to the inlet channel 301 through the inlet port 303 and becomes a space that guides the liquid to be tested that is introduced from the inlet port 303 to the connected through-holes 12 of the filtration portion 21 of the cancer cell-trapping metal filter member 10.

When the cancer cell-trapping device 3 is viewed from an upper side, the inlet port 303 of the cover member 31 is disposed at an outer position in relation to an observation region in which the filtration portion 21 is positioned, and the inlet channel 301 extends along an in-plane direction of the cancer cell-trapping metal filter 1. According to this configuration, when observing the filtration portion 21 of the cancer cell-trapping metal filter member 10 from the outside of the cancer cell-trapping device 3, it is possible to avoid presence of a visual-field blocking structure. Accordingly, the cancer cell-trapping device 3 can be directly and stably fixed on a stage of a microscope, and observation can be performed without disassembling the cancer cell-trapping device 3. In addition, the in-plane direction represents all directions in a plane of the cancer cell-trapping metal filter 1, and all directions along a plane parallel with the surface of the cancer cell-trapping metal filter 1. In addition, "along an in-plane direction" represents a direction that makes an angle of less than 60° with respect to the in-plane direction, preferably less than 45°, and still more preferably less than 30°.

It is preferable that the inlet channel 301 be formed from a resin such as polypropylene (PP). It is preferable that the inlet channel 301 have an outer diameter of 0.4 mm to 2.4 mm and an inner diameter of 0.2 mm to 2.2 mm. In addition, it is preferable that the inlet port 303 connected to the introduction region 311 have an inner diameter of 0.4 mm to 2.5 mm.

In addition, in the casing 33, the accommodation member 32 includes the outlet channel 302 and an outlet port 304. The outlet channel 302 is disposed at a side surface of the accommodation member 32. In addition, a mounting region 312 and a discharge region 313 are provided inside the accommodation member 32. The mounting region 312 is a region in which the cancer cell-trapping metal filter 1 is mounted. The discharge region 313 is provided on a lower side of the mounting region 312 of the cancer cell-trapping metal filter 1 and serves as a space for introducing the liquid to be test, which passed through the cancer cell-trapping metal filter 1, to the outlet channel 302.

The mounting region 312 is a recessed portion that is provided on an upper surface side of the accommodation member 32 in correspondence with the shape of the cancer cell-trapping metal filter member 10. The discharge region 313, which has a size smaller than that of the mounting region 312 when viewed from an upper surface side, is provided as a recessed portion at the central portion of the mounting region 312. A protrusion 314 is provided on a peripheral edge side of the mounting region 312 (in a region in which the discharge region 313 is not formed). The protrusion 314 is provided in correspondence with the positioning hole 23 that is provided in the connection portion 22 of the cancer cell-trapping metal filter member 10, and has a function as a positioning member during mounting of the cancer cell-trapping metal filter member 10 on the accommodation member 32. As described above, according to the configuration in which the cancer cell-trapping metal filter member 10 is mounted on the accommodation member 32 by using the protrusion 314 provided to the accommodation member, installation of the cancer cell-trapping metal filter member 10 becomes easy during assembly of a device, and thus production efficiency is improved. The thickness of the mounting region 312 corresponds to the thickness of the cancer cell-trapping metal filter. That is, it is preferable that the thickness of the mounting region 312 be 3 μm to 100 μm.

Figure 9:
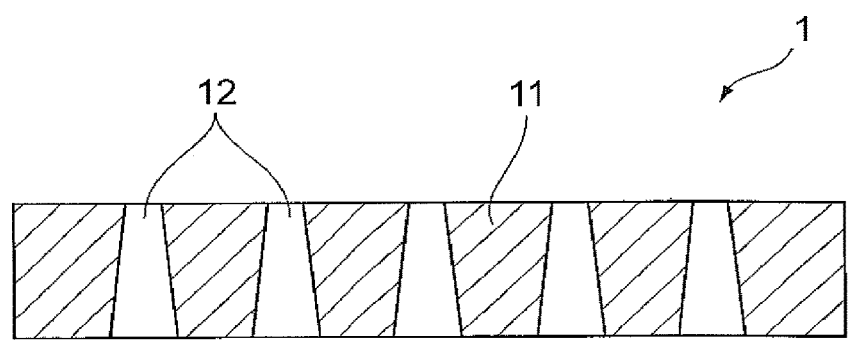
FIG. 9 is a cross-sectional view, which is taken along line IX-IX, of the cancer cell-trapping metal filter 1 shown in FIG. 1.

Here, the shape of the connected through-holes 12 of the cancer cell-trapping metal filter that is mounted on the mounting region 312 may be different between an upper surface side and a lower surface side. FIG. 9 is a IX-IX cross-sectional view of the cancer cell-trapping metal filter 1 shown in FIG. 1. In a case of manufacturing the cancer cell-trapping metal filter 1 according to the following method of manufacturing the cancer cell-trapping metal filter 1, as shown in FIG. 9, a length of a short side of each of the connected through-holes 12 on one surface side becomes longer than that of a length of a short side of the connected through-hole 12 on the other surface side. In this case, it is preferable that a surface in which the length of the short side of the connected through-hole 12 is smaller be disposed on a cover member 31 side, that is, on an upstream side of the flow path of the liquid to be tested. In this manner, when the surface in which the length of the short side is shorter is set as the upstream side, it is possible to suppress clogging due to blood components included in the liquid to be tested. It is preferable that a difference the length of the short side of the connected through-hole 12 on one surface side and the length of the short side of the connected through-hole 12 on the other surface side be 0.1 μm to 2.5 μm, more preferably 0.1 μm to 2.0 μm, and still more preferably 0.1 μm to 1.5 μm. In addition, when designing the size of the hole diameter of the connected through-hole, a definition is made based on the length of the short side on a shorter side.

When viewed from an upper side of the cancer cell-trapping device 3, the discharge region 313, which is provided on a lower side of the central portion of the casing 33, is provided on a lower side of the filtration portion 21 of the cancer cell-trapping metal filter 1 mounted on the accommodation member 32 to include the entirety of the filtration portion 21 provided with the connected through-holes 12 in the cancer cell-trapping metal filter member 10. The discharge region 313 is connected to the outlet channel 302 and becomes a space that discharges the liquid to be tested, which passed the connected through-holes 12 of the filtration portion 21 of the cancer cell-trapping metal filter member 10, from the outlet channel 302.

It is preferable that the outlet channel 302 be formed from a resin such as polypropylene (PP). It is preferable that the outlet channel 302 have an outer diameter of 0.4 mm to 2.4 mm and an inner diameter of 0.2 mm to 2.2 mm. In addition, it is preferable that the outlet port 304 connected to the discharge region 313 have an inner diameter of 0.4 mm to 2.5 mm.

When viewed from an upper side of the cancer cell-trapping device 3, the outlet channel 302 and the outlet port 304 of the accommodation member 32 are disposed at an outer position in relation to an observation region in which the filtration portion 21 is positioned, and the outlet channel 302 extends along an in-plane direction of the cancer cell-trapping metal filter 1. According to this configuration, when observing the filtration portion 21 of the cancer cell-trapping metal filter member 10 from the outside of the cancer cell-trapping device 3 through the upper surface, it is possible to avoid presence of a visual-field blocking structure. Accordingly, the cancer cell-trapping device 3 can be directly and stably fixed on a stage of a microscope, and observation can be performed without disassembling the cancer cell-trapping device 3.

As described above, the introduction region 311 that is provided on an upper side of the cancer cell-trapping metal filter member 10 and the discharge region 313 that is provided on a lower side of the cancer cell-trapping metal filter member 10 are preferably formed to include the entirety of the filtration portion 21 provided with the connected through-holes 12 in the cancer cell-trapping metal filter 1.

It is preferable that the cover member 31 and the accommodation member 32, which form the casing 33 in the cancer cell-trapping device 3, be welded to each other. The welding represents a method in which materials themselves are partially melted at a high temperature and the materials are directly bonded to each other. The welding may be called fusion, thermal bonding, or heat sealing. Examples of a welding method include thermal welding, ultrasonic welding, high-frequency welding, and the like. After placing the cancer cell-trapping metal filter 1 on the mounting region 312, the periphery of the mounting region 312 is welded by a heat treatment, an ultrasonic treatment, and the like to fix the cover member 31 and the accommodation member 32, thereby reliably attaining airtightness of the cancer cell-trapping device. Accordingly, when the cell-dispersed liquid that becomes the liquid to be tested is introduced into the cancer cell-trapping device, it is possible to secure a high liquid sealing property. In addition, the bonding by the welding is excellent in productivity when considering that a bonding process can be completed within a short time. Among the above-described welding methods, the ultrasonic welding or the high-frequency welding is particularly preferable when considering that a necessary site of the material can be melted within a short time.

In addition, in the above-described embodiment, a configuration in which the cancer cell-trapping metal filter member 10 is mounted on the accommodation member 32 has been described, but this configuration may be appropriately changed.

Figure 10A:
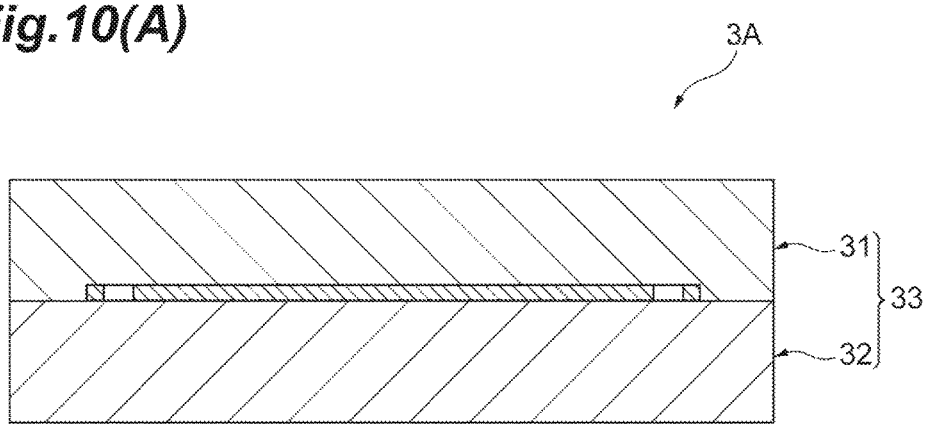
FIGS. 10(A) and 10(B) are views illustrating a modification example of the cancer cell-trapping device, and FIGS. 10(A) and 10(B) correspond to FIGS. 8(A) and 8(B).
Figure 10B:
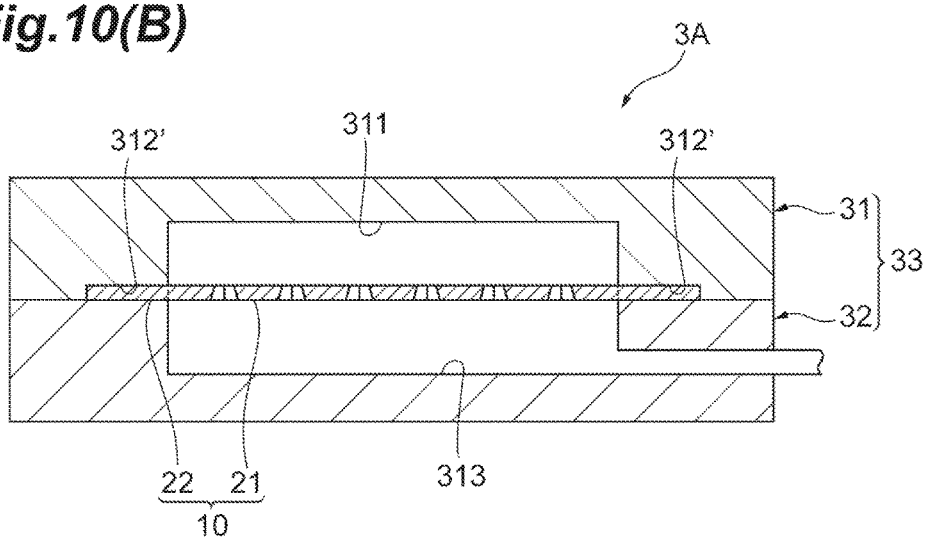

FIGS. 10(A) and 10(B) are views illustrating a modification example of the cancer cell-trapping device, and correspond to FIGS. 8(A) and 8(B). A cancer cell-trapping device 3A shown in FIGS. 10(A) and 10(B) is different from the cancer cell-trapping device 3 shown in FIGS. 8(A) and 8(B) in that a mounting region 312' that is a recessed portion to which the cancer cell-trapping metal filter member 10 is fixed is provided on a cover member 31 side. As described above, a configuration inside the cancer cell-trapping device can be appropriately changed without limitation to the above-described embodiment.

A method of using the above-described cancer cell-trapping device 3 will be described.

As the cell-dispersed liquid, blood, a lymph fluid, a tissue fluid, umbilical cord blood, and the like, which are filled in the bone marrow, the spleen, the liver, and the like, may be used. However, it is most convenient to use peripheral blood that circulates in the body. Detection of presence of the CTC in the peripheral blood is useful to determine progress in the condition of cancer.

When detecting whether or not the CTC is present in the cell-dispersed liquid, the cell-dispersed liquid is introduced to the inlet channel 301 of the cancer cell-trapping device, passes through the cancer-cell trapping metal filter member 10, and is discharged from the outlet channel 302. According to this, cells including the CTC are concentrated on the cancer cell-trapping metal filter 1, and it may be confirmed whether or not the CTC is present in the concentrated cells. For introduction of the cell-dispersed liquid into the inlet channel 301, a method in which pressurization or decompression is performed, a method in which a peristaltic pump is used, and the like may be exemplified. In addition, for example, in a case of concentrating the CTC from blood of 1 mL, an area of a trapping region (an area of the filtration portion 21) of the cancer cell-trapping metal filter member 10 is appropriately 25 mm$^2$ to 1000 mm$^2$.

In a case of concentrating the CTC by the above-described method, not only the CTC, but also blood cells such as a white blood cell are simultaneously concentrated. Therefore, it is necessary to confirm whether or not epithelial cells derived from a cancer primary lesion are included in the collected cells. For example, confirmation of the epithelial cells can be performed by concentrating the CTC according to the above-described method and by dying the concentrated CTC with an antibody against a fluorescent-labeled epithelial cell marker. Examples of the antibody against the epithelial cell marker include an anti-cytokeratin antibody, and the like.

For example, the dying and observation of the concentrated cells may be performed as follows. A formalin solution is introduced from the inlet channel 301 of the cancer cell-trapping device 3 after concentration of the cells to protect and fix a cell state on cancer cell-trapping filter 1. After a washing treatment, a dying liquid is allowed to penetrate into the cells by using a non-ionic surfactant. Then, an anti-cytokeratin antibody solution is introduced into the inside of the cancer cell-trapping device 3, and then the cancer cell-trapping device 3 is left as is for a predetermined time. Subsequently, a washing buffer is introduced to the inlet channel 301 of the cancer cell-trapping device to wash and remove an unreacted antibody. Subsequently, the cancer cell-trapping device 3 is directly fixed to a stage of a microscope to perform fluorescent microscope observation. Before introducing the antibody solution to the cancer cell-trapping device 3, a blocking buffer that suppresses a non-specific reaction of the antibody may be introduced.

In addition, the confirmation of the CTC may be performed by collecting the cells that are concentrated by the above-described method and by performing gene analysis. For example, the cell collection may be performed by introducing a buffer from the outlet channel side of the cancer cell-trapping device and by collecting the buffer from the inlet channel side. For example, confirmation of the CTC may be performed by analyzing a mutation in genes such as p53, K-RAS, H-RAS, N-RAS, BRAF, and APC. In addition, results of the gene analysis may be used in the subsequent determination of a therapeutic strategy of a patient and the like. In addition, the confirmation of the CTC may be performed by measuring telomerase activity of the cells that are concentrated by the above-described method, and the like.

After completion of the detection of whether or not the CTC is present in the cell-dispersed liquid, the cancer cell-trapping device 3 may be used again by introducing a buffer from the outlet channel 302 side of the cancer cell-trapping device and by discharging the buffer from the inlet channel 301 side to wash and remove the cells that are trapped in the cancer cell-trapping metal filter 1.

(Method of Manufacturing Cancer Cell-Trapping Metal Filter)

Next, a method of manufacturing the above-described cancer cell-trapping metal filter 1 will be described with reference to FIGS. 11 and 12. The method of manufacturing the cancer cell-trapping metal filter 1 according to this embodiment includes a process of laminating a photoresist on metal foil, a process of overlapping a photomask including a wave-shaped light-transmitting portion on the photoresist layer and exposing the photoresist layer, a process of removing a non-exposed portion of the photoresist layer by development to form photoresist patterns, a process of performing metal plating between the photoresist patterns to form metal plating patterns having a height lower than a height of the photoresist patterns, a process of removing the metal foil by chemical dissolution to obtain a structure including the metal plating patterns and the photoresist patterns, and a process of removing the photoresist patterns from the structure to obtain the metal plating patterns having a through-hole corresponding to the light-transmitting portion. Hereinafter, respective processes will be described.

Figure 11A:
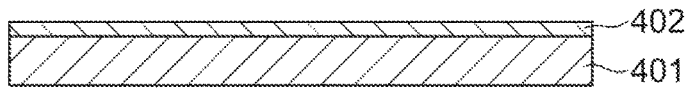
FIGS. 11(A)-11(H) are views illustrating a method of manufacturing the cancer cell-trapping metal filter.

FIG. 11(A) illustrates a state in which metal foil 402 is laminated on a carrier layer 401. In a lamination process shown in FIG. 11(B), a photoresist 403 formed from a photosensitive resin composition is formed on the metal foil 402. Subsequently, in an exposure process shown in FIG. 11(C), the photoresist 403 is irradiated with active light beams (UV light) through a photomask 404 to optically cure an exposed portion, thereby forming a cured material of the photoresist. Subsequently, in a development process shown in FIG. 11(D), the photoresist 403 other than the cured material is removed to form photoresist patterns 403a (403b in FIG. 11(D) indicates a portion in which an uncured photoresist is removed and a plating layer is to be formed in the subsequent process). Subsequently, in a plating process shown in FIG. 11(E), a plating layer 405 is formed on the metal foil 402 on which the photoresist patterns 403a composed of the cured material are formed. Subsequently, as shown in FIG. 11(F), the carrier layer 401 and the metal foil 402 are peeled from each other. Subsequently, in a dissolution process shown in FIG. 11(G), the metal foil 402 is removed by a chemical dissolution. As a result, the photoresist patterns 403a composed of the cured material of the photoresist, and the plating layer 405 remain. Subsequently, in a peeling process shown in FIG. 11(H), the photoresist patterns 403a composed of the cured material of the photoresist are removed to collect a metal filter constituted by the plating layer 405. In the metal filter, connected through-holes 406 are formed.

FIGS. 12(A) to 12(G) are process diagrams illustrating another method of manufacturing the cancer cell-trapping metal filter 1. The manufacturing method shown in FIG. 12 is different from the manufacturing method shown in FIG. 11 in that a metal substrate 402' is used instead of the metal foil 402. In this case, the cancer cell-trapping metal filter 1 can be manufactured by the same method as the manufacturing method shown in FIG. 11 except that the process of peeling the metal foil 402 and the carrier layer 401 from each other as shown in FIG. 11(F) is not present. However, the substrate 402' is thicker than the metal foil 402, the amount of the chemical dissolving agent that is used in the process of removing the substrate 402' by the chemical dissolution and chemical dissolution time during the dissolution process increase in comparison to the removal of the metal foil 402.

Hereinafter, the respective processes will be described in more detail.

(Lamination Process)

First, a state in which the metal foil 402 is laminated on the carrier layer 401 is illustrated. As the metal foil 402, metal foil capable of being removed by etching can be used. Specifically, copper foil, nickel foil, nickel-chrome alloy foil, and the like are used, but the copper foil is preferable. The copper foil can be easily removed by chemical etching, and adhesion with the photoresist is superior to other materials. When using a laminated body which is obtained by bonding the metal foil 402 to the carrier layer 401 constituted by copper clad laminated plate to a certain degree capable of being peeled in the subsequent process, workability and handabilty during processes of manufacturing the cancer cell-trapping metal filter are excellent, and this is preferable. As the above-described configuration, specifically, Peelable Copper Foil (manufactured by Hitachi Chemical Co., LTD.) may be used. The Peelable Copper Foil represents copper foil constituted by at least two layers of ultrathin copper foil and a carrier layer.

Figure 11B:

FIG. 11(B) is a view illustrating a state in which the photoresist 403 composed of the photosensitive resin composition is formed on the metal foil 402. As the photoresist 403, all of a negative type photoresist and a positive type photoresist may be used, but the negative type photoresist is preferable. As the negative type photoresist, a photoresist including at least a binder resin, a photopolymerizable compound having an unsaturated bond, and a photopolymerization initiator is preferable. In addition, in a case of using the positive type photoresist, in the photoresist layer, solubility of a portion exposed by irradiation of the active light beams with respect to a developing solution increases, and thus the exposed portion is removed in the development process. Hereinafter, a case of using the negative type photoresist will be described.

The thickness of the cancer cell-trapping metal filter 1 that can be finally obtained is equal to or less than the thickness of the photoresist patterns. Accordingly, it is necessary to form a photoresist layer having a film thickness that is appropriate for the thickness of a target metal filter. For example, in a case of manufacturing a metal filter having a thickness less than 15 µm, it is preferable to use a photoresist having a film thickness of 15 µm. In addition, in a case of manufacturing a metal filter having a thickness that is more than 15 µm and less than 25 µm, it is preferable to use a photoresist having a film thickness of 25 µm. In addition, as the hole diameter of the connected through-holes decreases, it is preferable to use a photoresist having a small film thickness.

For example, the lamination of the photoresist 403 on the metal foil 402 is performed by removing a protective film of a sheet-shaped photosensitive element constituted by a supporting film, a photoresist, and the protective film, and compressing the photoresist 403 on the metal foil 402 while heating the photoresist 403. According to this, a laminated body in which the metal foil 402, the photoresist 403, and the supporting film, and these components are sequentially laminated can be obtained.

It is preferable that the lamination process be performed under a decompressed atmosphere in consideration of adhesion and followability. On the other hand, conditions such as a heating temperature and a pressure with respect to the photoresist 403 and/or the metal foil 402 during compression are not particularly limited. However, the heating is preferably performed at a temperature of 70° C. to 130° C., and the compression is preferably performed at a pressure of approximately 100 kPa to 1000 kPa. In addition, during the compression of the photoresist, the metal foil may be subjected to a preheating treatment to improve lamination properties. In addition, the supporting film may have a photomask function. In this case, the supporting film may be used as the photomask as is in the subsequent process, or the supporting film is peeled otherwise before overlapping the photomask in the subsequent process (Exposure Process)

Subsequently, the exposure process will be described. The photomask 404 having a wave-shaped light-transmitting portion is overlapped on the photoresist 403 on the metal foil 402, and then the photoresist 403 is irradiated with active light beams to optically cure an exposed portion, thereby forming the cured material 403a of the photoresist.

The photomask includes a wave-shaped light-transmitting portion. The light-transmitting portion has a wave shape obtained by connecting ends of a plurality of rectangles or rectangles with rounded corners to make a predetermined angle, or by connecting ends in such a manner that semicircles are alternately opposite to each other. This shape becomes a shape of the through-holes in the cancer cell-trapping metal filter 1.

As an exposure method, a method (mask exposure method) in which active light beams are emitted onto an image through a negative or positive mask pattern called artwork may be exemplified. In addition, a method in which the active light beams are emitted in an image shape by a direct drawing exposure method such as a laser direct imaging (LDI) exposure method and a digital light processing (DLP) exposure method may be employed.

As a light source of the active light beams, a known light source may be used, and examples of the light sources include light sources such as a carbon arc lamp, a mercury vapor arc lamp, a high-pressure mercury lamp, a xenon lamp, gas laser such as argon laser, solid laser such as YAG laser, and semiconductor laser which are capable of effectively radiating ultraviolet rays, visible rays, and the like.

It is preferable that a wavelength (exposure wavelength) of the active light beams be set in a range of 350 nm to 410 nm, and more preferably in a range of 390 nm to 410 nm. It is preferable that the exposure be performed in vacuo at a pressure of 600 mmHg or less. It is preferable that the exposure be performed in an amount of exposure in a range of 0.01 J/cm$^2$ to 10 J/cm$^2$, and more preferably in a range of 0.01 J/cm$^2$ to 5 J/cm$^2$.

Figure 11C:
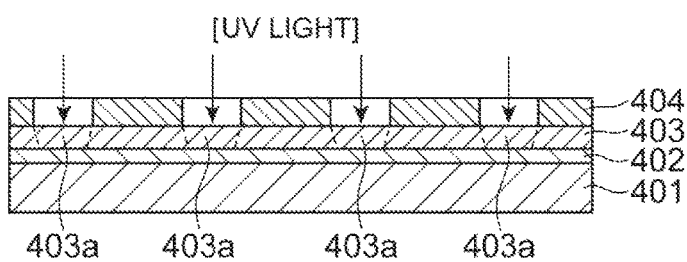
Figure 11D:
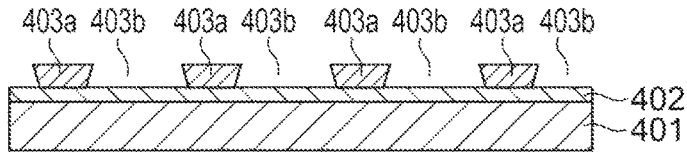
Figure 11E:
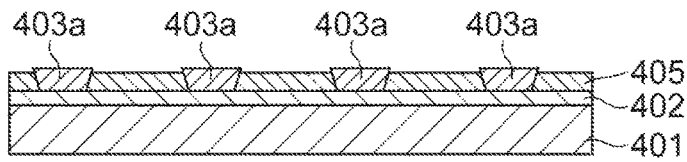
Figure 11F:
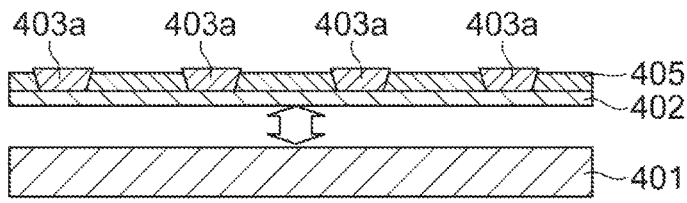
Figure 11G:
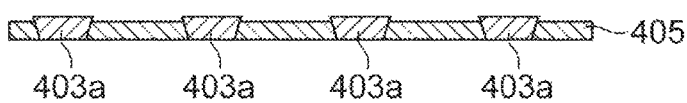

In addition, as shown in FIG. 11(C), the active light beams are emitted from an upper side of the photomask 404, and an upper surface side of the photoresist 403 is affected by the active light beams and tends to be cured, and a lower surface side of the photoresist 403 on a metal foil 402 side is less likely to be cured in comparison to the upper surface side. As a result, the cured material 403a can be obtained in a shape in which the top of the cured material 403a on an upper side is large, and as it goes toward the bottom on a lower side, the size of the cured material 403a decreases.

(Process of Forming Photoresist Pattern)

In the photoresist 403, a portion of the photoresist other than the cured material is removed from the metal foil 402 to form the photoresist patterns 403a constituted by the cured material of the photoresist on the metal foil 402. In a case where the supporting film or the photomask is present on the photoresist, the removal (development) of the portion of the photoresist other than the cured material is performed after removing the supporting film or the photomask. As a development method, wet development and dry development may be exemplified, but the wet development is widely used.

In the case of the wet development, a developing solution that corresponds to the photoresist is used, and development is performed by a known development method. Examples of the development method include a dipping method, a paddle method, a spraying method, and methods using brushing, slapping, scrapping, fluctuation dipping, and the like, and a high-pressure spraying method is most preferable from the viewpoints of an improvement in resolution. The development may be performed in combination of two or more methods among the above-described development methods.

Examples of the developing solution include an alkaline aqueous solution, an aqueous developing solution, an organic solvent-based developing solution, and the like. In a case of being used as the developing solution, the alkaline aqueous solution is safe and stable, and thus handability is excellent. Examples of a base of the alkaline aqueous solution that is used include alkali metal hydroxide such as hydroxides of lithium, sodium, or potassium; carbonate or bicarbonates of lithium, sodium, potassium, or ammonium; alkali metal phosphates such as potassium phosphate and sodium phosphate; alkali metal pyrophosphates such as sodium pyrophosphate and potassium pyrophosphate; and the like.

As the alkaline aqueous solution, a dilute solution of sodium carbonate of 0.1% by mass to 5% by mass, a dilute solution of potassium carbonate of 0.1% by mass to 5% by mass, a dilute solution of sodium hydroxide of 0.1% by mass to 5% by mass, a dilute solution of sodium tetraborate of 0.1% by mass to 4% by mass, and the like are preferable. pH of the alkaline aqueous solution is preferably set to a range of 9 to 11, and a temperature thereof is adjusted in accordance with alkali developability of the photoresist. A surface active agent, a defoaming agent, a small amount of organic solvent which promotes development, and the like may be mixed-in into the alkaline aqueous solution.

In addition, after removing the portion of the photoresist 403 other than the cured material by development to form the photoresist patterns 403a constituted by the cured material of the photoresist on the metal foil 402, heating at a temperature of approximately 60° C. to 250° C. or exposure with approximately 0.2 J/cm$^2$ to 10 J/cm$^2$ may be performed as necessary to further cure the photoresist patterns.

In the photoresist patterns, it is preferable that an aspect ratio (height/length of the short side) between the height of the photoresist patterns and the length of the short side thereof be 1 to 10, more preferably 2 to 7, and still more preferably 3 to 5. When the aspect ratio exceeds 10, the shape of the photoresist patterns becomes unstable, and thus the photoresist patterns tend to collapse. As a result, a yield ratio in manufacturing of the cancer cell-trapping metal filter decreases. On the other hand, when the aspect ratio is less than 1, effective CTC trapping may become difficult in the cancer cell-trapping metal filter, or handability of the cancer cell-trapping metal filter may deteriorate. As described above, in the photoresist patterns which have a wave shape obtained by connecting ends of rectangles or rectangles with rounded corners, or by connecting ends in such a manner that semicircles are alternately opposite to each other, the patterns are less likely to collapse during development, and thus productivity is excellent.

Here, a preferred shape in a case of forming the photoresist patterns having a wave shape obtained by connecting ends of rectangles or rectangles with rounded corners will be further described. In the photomask 404, when setting an extending direction of the wave-shaped light-transmitting portion is set as a longitudinal direction, in a case where a plurality of light-transmitting portions are disposed to be close to each other along a short direction perpendicular to the longitudinal direction of the light-transmitting portion, an intersecting portion (portion that becomes the top of the wave shape) in the photoresist patterns that are formed may be formed to have a corner that is further rounded in comparison to design of the light-transmitting portion of the photomask 404. This is because the developing solution cannot sufficiently penetrate between cured portions of the photoresist during development. Accordingly, in each of the photoresist patterns, when an intersection angle at the portion that becomes the top of the wave shape is set to 90° to 150°, the penetration of the developing solution can be sufficiently performed. In addition, the intersection angle of the photoresist pattern is calculated by the same method of calculating an intersection angle of the connection portion in the connected through-holes of the metal filter. That is, the intersection angle represents an angle that is smaller than 180° in angles made by central lines in a long-side direction of two rectangular patterns that constitute the top of the wave-shaped pattern (refer to FIG. 2(B)).

The photoresist patterns 403a obtained by the cured material are formed in such a manner that the bottom is slightly wider than the top. This is caused because the bottom is not sufficiently exposed in comparison to the top.

(Process of Forming Metal Plating pattern)

After the development process, metal plating is performed on the metal foil 402 to form the metal plating patterns 405. Examples of a plating method include solder platting, nickel plating, and gold plating. The plating layer finally becomes the metal filter, and the photoresist patterns are removed by the subsequent process to form the connected through-holes of the metal filter. Accordingly, it is important to perform the plating in a height lower than that of the photoresist patterns so as not to cover the photoresist patterns.

Examples of a kind of metal in the metal plating include a noble metal such as gold and silver, a base metal such as aluminum, tungsten, nickel, and chrome, and alloys of these metals, but there is no limitation to these. The metals may be used as an elementary substance, or may be used as an alloy with other metals or a metal oxide to apply functionality. Among these, it is preferable to use nickel and a metal including nickel as a main component in consideration of prevention of occurrence of corrosion and the like, and excellence in workability and cost. Here, the main component represents a component, which is included in the highest ratio, among materials.

In the metal plating patterns 405 that are formed as described above, the bottom is formed to be slightly wider than the top. This is because as described above, each of the photoresist patterns 403a has a shape in which the top is slightly wider than the bottom.

(Process of Obtaining Structure Including Metal Plating Pattern and Photoresist Pattern)

After forming the metal plating patterns 405, the metal foil 402 is chemically dissolved and is removed. According to this, it is possible to collect a structure including the metal plating patterns 405 which become the metal filter, and the photoresist patterns 403a without manual working (manual peeling). Accordingly, it is possible to manufacture the metal filter without causing damage such as a winkle, bending, a scratch, and curling, or minute deformation of the connected through-holes. As the chemical dissolving agent that dissolves the metal foil, MEC Bright SF-5420B (product name, manufactured by MEC Co., Ltd.), Copper selective etchant-CSS (manufactured by NIHON KAGAKU SANGYO CO., LTD.), and the like may be used.

(Process of Removing Photoresist Pattern)

Subsequently, for example, the resist pattern 403a is removed by an alkaline aqueous solution that is stronger than the alkaline aqueous solution that is used in the development. As the strong alkaline aqueous solution, for example, it is preferable to use a sodium hydroxide aqueous solution or potassium hydroxide aqueous solution of 1% by mass to 10% by mass, and more preferably a sodium hydroxide aqueous solution or potassium hydroxide aqueous solution of 1% by mass to 5% by mass. It is possible to collect only the metal plating patterns 405 by removing the resist patterns (cured materials of the photoresist). The metal plating patterns 405 become the metal filter.

Examples of a method of removing the resist pattern include a dipping method, a spraying method, a method using ultrasonic waves, and the like, and these methods may be used alone or in combination.

Figure 11H:
Figure 12A:
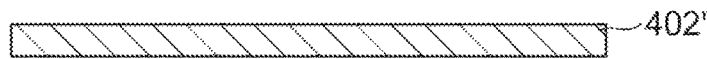
FIGS. 12(A)-(G) are views illustrating another method of manufacturing the cancer cell-trapping metal filter.
Figure 12B:
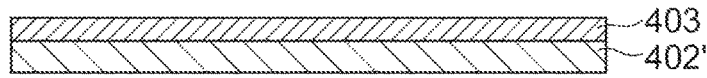
Figure 12C:
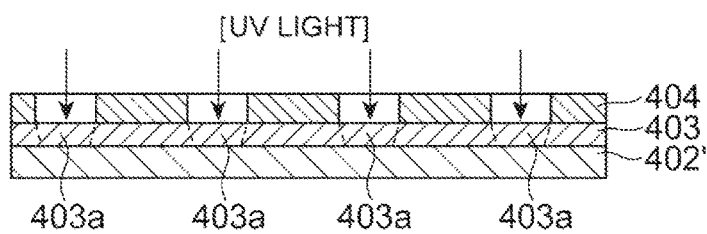
Figure 12D:
Figure 12E:
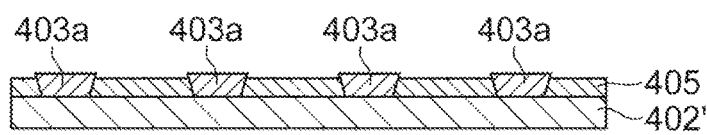
Figure 12F:
Figure 12G:

Through the above-described processes, it is possible to obtain the cancer cell-trapping metal filter according to this embodiment. In the cancer cell-trapping metal filter that is obtained through the above-described processes, as shown in FIG. 11(H) and the like, the length of the short side of the connected through-holes in the upper surface becomes larger than the length of the short side of the connected through-holes in the lower surface in correspondence with an inclination of the cured materials 403a. At this time, a difference in the length of the short side of the connected through-holes in the lower surface and the length of the short side of the connected through-holes in the upper surface is preferably 0.1 μm to 2.5 μm, more preferably 0.1 μm to 2.0 μm, and still more preferably 0.1 μm to 1.5 μm.

(Method of Manufacturing Cancer Cell-Trapping Metal Filter Sheet)

Next, a method of manufacturing the cancer cell-trapping metal filter sheet according to this embodiment will be described.

The method of manufacturing the cancer cell-trapping metal filter sheet according to this embodiment includes a process of laminating a photoresist on metal foil, a process of overlapping a photomask including a plurality of blocks of wave-shaped light-transmitting portions on the photoresist and exposing the photoresist, a process of removing an uncured portion of the photoresist by development to form photoresist patterns, a process of performing metal plating between the photoresist patterns to form metal plating patterns having a height lower than a height of the photoresist patterns, a process of removing the metal foil by chemical dissolution to obtain a structure including the metal plating patterns and the photoresist patterns, and a process of removing the photoresist patterns from the structure to obtain the metal plating patterns. The method of manufacturing the cancer cell-trapping metal filter sheet and the method of manufacturing the cancer cell-trapping metal filter are different as follows. That is, the method of manufacturing the cancer cell-trapping metal filter sheet is a method of manufacturing a sheet in which a plurality of sheets of cancer cell-trapping metal filters are connected at a connection portion, and thus the shape of the photomask has a shape corresponding to the sheet. In addition, a resist pattern corresponding to the positioning hole, which is provided in the connection portion, is provided. Accordingly, materials and manufacturing conditions which are appropriately used during manufacturing of the cancer cell-trapping metal filter sheet are the same as that of the cancer cell-trapping metal filter. In addition, the size of the cancer cell-trapping metal filter sheet is determined in correspondence with the number of sheets of the cancer cell-trapping metal filters that are manufactured at a time, and thus the size is appropriately changed.

In addition, in a case of using parts of the cancer cell-trapping metal filter sheet as the cancer cell-trapping metal filter, a region that becomes the connection portion of the cancer cell-trapping metal filter sheet is cut to individually separate the filtration portions, and these filtration portions are used as the cancer cell-trapping metal filter.

(Method of Manufacturing Cancer Cell-Trapping Device)

Next, a method of manufacturing the cancer cell-trapping device according to this embodiment will be described. The cancer cell-trapping device 3 is formed by interposing and fixing the cancer cell-trapping metal filter member 10 between the cover member 31 including the inlet channel 301 and the accommodation member 32 including the outlet channel 302. At this time, the cancer cell-trapping metal filter member 10 is mounted between the cover member 31 and the accommodation member 32 in such a manner that a surface in which a hole diameter of the connected through-hole is small is positioned on a cover member 31 side (upstream side).

The cover member 31 and the accommodation member 32 are welded by ultrasonic welding. At this time, it is preferable that a horn of a welding machine have a shape capable of uniformly compressing an outer periphery of an upper surface of the cover member. When using the horn having this shape, the surfaces of the cover member 31 and the accommodation member 32 which come into contact with each other can be uniformly welded, and thus it is possible to realize a structure from which the liquid to be tested is not leaked. In addition, the ultrasonic welding may be carried out by using a welding machine such as W5040-20 manufactured by NIPPON FUTURE CO., LTD. under conditions of 10 kHz to 30 kHz, 0.1 MPa to 0.5 MPa, and 0.05 seconds to 1.5 seconds.

In the cancer cell-trapping device, it is preferable that the length of the short side of the connected through-holes of the filter on a cover member side be shorter than the length of the short side of the connected through-holes on an accommodation member side. According to this structure, clogging by the blood components may be less likely to occur.

In addition, it is preferable that the cancer cell-trapping device 3 have the following structure. That is, a protrusion that fixes the filter is provided to at least one of the cover member and the accommodation member, and the protrusion is inserted into the positioning hole on an outer side of a region in which the connected through-holes of the filter are formed, and thus the filter is fixed between the accommodation member and the cover member of a cartridge. According to this structure, installation of the filter becomes easy during device assembly, and thus production efficiency is improved.

With regard to the connected through-holes 12 of the cancer cell-trapping metal filter member 10, the hole diameter on an outlet side (downstream side) is wider than the hole diameter on an inlet side (upstream side), and thus a filtered material such as blood cells that passed through the connected through-holes 12 at once are less likely to stay in the holes. Accordingly, occurrence of clogging in the filter can be reduced, and thus a pressure loss does not occur. As a result, the number of the blood cells that remain on the filter, particularly, white blood cells, and thus it is possible to improve separation accuracy of the filter.

As described above, according to the cancer cell-trapping metal filter 1, the cancer cell-trapping metal filter sheet 2, and the cancer cell-trapping device 3 using the cancer cell-trapping metal filter (in this embodiment, the cancer cell-trapping metal filter member 10 including the filtration portion 21 that functions as the cancer cell-trapping metal filter) according to this embodiment, the opening of the connected through-holes has a wave shape, and thus, it is possible to extract the CTC from other components by using the hole diameter on a short-side side (the length of the short side), and it is possible to make the connected through-holes be closer to each other due to the wave shape while maintaining a CTC trapping ability. Accordingly, it is possible to further improve an opening ratio in the cancer cell-trapping metal filter. As a result, even in the cancer cell-trapping device 3, the CTC trapping ability can be improved.

In addition, according to the method of manufacturing the cancer cell-trapping metal filter and the method of manufacturing the cancer cell-trapping metal filter sheet, it is possible to reduce a possibility that the photoresist patterns for formation of the wave-shaped connected through-holes collapse or are peeled-off during manufacturing, and thus it is possible to attain an effect of obtaining the cancer cell-trapping metal filter or the cancer cell-trapping metal filter sheet which has a high opening ratio, and of improving a yield ratio.

Hereinbefore, the embodiment of the invention has been described, but the cancer cell-trapping metal filter, the cancer cell-trapping metal filter sheet, and the cancer cell-trapping device according to this embodiment are not limited to the above-described embodiment, and various kinds of changes can be made.

For example, the cancer cell-trapping metal filter according to the invention may be applied to all of body fluids including cells which contain a CTC, particularly, a seeded and micro-metastatic CTC.

Specifically, examples of the blood fluids include a lymph fluid, urine, sputum, ascites, effusions, an amniotic fluid, an aspirate, an internal organ lavage fluid, an intestinal lavage fluid, a lung lavage fluid, a bronchial lavage fluid, a bladder lavage fluid, and feces, and particularly bone marrow, and blood. These cell-containing blood fluids can be directly filtered and cells can be concentrated. However, as a process of preparing a cell-containing blood fluid at first, components that do not contain cells may be removed in advance by density gradient centrifugation and the like.

EXAMPLES

Hereinafter, the invention will be described in more detail on the basis of Examples, but the invention is not limited to the following Examples.

First, an evaluation method in the following Examples will be described at first, a method of manufacturing the cancer cell-trapping metal filter according to Examples and Comparative Examples will be described, and evaluation results according to the above-described evaluation method will be described together.

<Evaluation Method>

(Method of Measuring Intersection Angle)

The intersection angle was obtained by observing and photographing a connected portion between ends in each connected through-hole of the cancer cell-trapping metal filter or the cancer cell-trapping metal filter sheet by a 3D Real Surface View Microscope (VE-8800 manufactured by KEYENCE CORPORATION), and by measuring an angle which is made when central lines of the connected through-holes in a long side direction intersect each other and which is smaller than 180°.

(Method of Measuring Opening Ratio)

The opening ratio was obtained as follows. A mask film having an opening corresponding to an area of a region functioning as a filter was provided between a light-emitting unit and a light-receiving unit of a double-beam spectrometer (trade name: 20-10 type, manufactured by Hitachi, LTD.), and an average value of absorbance of visible rays of 400 nm to 800 nm was obtained. Then, the cancer cell-trapping metal filter is provided between the light-emitting unit and the light-receiving unit, and an average value of absorbance of visible rays of 400 nm to 800 nm was obtained. A ratio (%) of the absorbance of the cancer cell-trapping metal filter to the absorbance of the area of the region functioning as a filter was obtained as the opening ratio.

In addition, the measurement of the opening ration was performed by using a surface in which the hole diameter of the connected through-holes was small <Manufacturing Method and Evaluation Result of Examples and Comparative Examples>

Example 1

A photoresist (PHOTEC RD-1225 having a thickness of 25 μm, manufactured by Hitachi Chemical Co., LTD.) was laminated to a one surface of a substrate of 250 mm square (MCL-E679F: a substrate obtained by bonding peelable copper foil to a surface of MCL, manufactured by Hitachi Chemical Co., LTD.). The lamination was performed under conditions a rolling temperature of 90° C., a pressure of 0.3 MPa, a conveyor speed of 2.0 m/minute.

Next, a glass mask having the following configuration was prepared. In a single wave-shaped light-transmitting portion, two light-transmitting portions having a rectangular shape with rounded corners in which a length of a short side was 10 μm and a length of a long side was 30 μm were connected at ends to be adjacent to each other. In addition, 100 pieces of the light-transmitting portions were arranged in the same direction along a short direction (Y-axis direction in FIG. 1) perpendicular to the longitudinal direction (X-axis direction in FIG. 1) in which the wave-shaped light-transmitting portion extends, and 100 rows of the light-transmitting portions were arranged along the longitudinal direction. An intersection angle of the two light-transmitting portions having a rectangular shape with rounded corners was 90°, and the shortest distance between adjacent light-transmitting portions was 10 μm in the short direction (Y-axis direction in FIG. 1) perpendicular to the longitudinal direction in which the light-transmitting portion extends, and was 10 μm in the longitudinal direction (X-axis direction in FIG. 1) in which the light-transmitting portion extends. The 5000 light-transmitting portions become a single filtration portion to be formed later. 10×10 filtration portions were arranged along a vertical direction and a horizontal direction. At this time, a connection portion was provided between the filtration portions adjacent to each other, and a width of the connection portion was set to 10 mm. The glass mask was placed on a photoresist lamination surface of the substrate. At this time, a surface side of the glass mask, in which the light-transmitting portions were provided, was set to face the photoresist lamination surface.

Next, ultraviolet rays were emitted in an exposure amount of 50 mJ/cm$^2$ by an ultraviolet irradiation device from an upper side of the glass mask in vacuo at a pressure of 600 mmHg or less.

Next, development was performed with a 1.0% sodium carbonate aqueous solution to form photoresist patterns, in which a photoresist having a rectangular shape with rounded corners stands vertically, on the substrate. Nickel plating was performed with respect to a copper exposed portion of the substrate to which the photoresist patterns were provided by using a nickel plating solution prepared to have pH adjusted to 4.5 (a solution temperature was set to 55° C., and a treatment time was set to 20 minutes). A composition of the nickel plating solution is shown in Table 1.

TABLE 1

| Composition of plating solution | Concentration(g/L) |
|---|---|
| Nickel sulfamate | 400 |
| Nickel chloride | 5 |
| Boric acid | 30 |

The nickel plating layer was peeled from the substrate together with the peelable copper foil, and the peelable copper foil was removed by chemical etching (MEC Bright SF-5420B, manufactured by MEC Co., Ltd.) during a stirring treatment at a temperature of 40° C. for approximately 150 minutes, thereby taking out a structure constituted by the metal plating patterns and the photoresist patterns.

Finally, the photoresist patterns that remained on the structure constituted by the metal plating patterns and the photoresist patterns were removed by an ultrasonic treatment (P3 Poleve, Henkel) at a temperature of 60° C. for approximately 40 minutes, thereby preparing the cancer cell-trapping metal filter according to Example 1. In the cancer cell-trapping metal filter according to Example 1, the photoresist patterns did not collapse during a manufacturing process, and damage such as a winkle, bending, a scratch, and curling was not present in the filter that was completed. The thickness of the cancer cell-trapping metal filter was 23 μm. In addition, the length of a short side of each connected through-hole was 9.6 μm on an upper surface side (on a short length side of the short side) of the cancer cell-trapping metal filter, and 9.8 μm on a lower surface side (on a long length side of the short side). In addition, the opening ratio of the cancer cell-trapping metal filter according to Example 1 was 22.7%.

Example 2

A photoresist (PHOTEC RD-1225 having a thickness of 25 μm, manufactured by Hitachi Chemical Co., LTD.) was laminated to a one surface of a substrate of 250 mm square (MCL-E679F: a substrate obtained by bonding peelable copper foil to a surface of MCL, manufactured by Hitachi Chemical Co., LTD.). The lamination was performed under conditions a rolling temperature of 90° C., a pressure of 0.3 MPa, a conveyor speed of 2.0 m/minute.

Next, a glass mask having the following configuration was prepared.

In a single wave-shaped light-transmitting portion, three light-transmitting portions having a rectangular shape with rounded corners in which a length of a short side was 8 µm and a length of a long side was 35 µm were continuously connected at ends. In addition, 100 pieces of the light-transmitting portions were arranged in the same direction along a short direction (Y-axis direction in FIG. 1) perpendicular to the longitudinal direction (X-axis direction in FIG. 1) in which the wave-shaped light-transmitting portion extends, and 30 rows of the light-transmitting portions were arranged along the longitudinal direction. An intersection angle of the light-transmitting portions, which are connected to be adjacent to each other and which have a rectangular shape with rounded corners, was 120°, and intersection directions between adjacent connected portions were different from each other. The shortest distance between adjacent light-transmitting portions was 12 µm in the short direction (Y-axis direction in FIG. 1) perpendicular to the longitudinal direction in which the light-transmitting portion extends, and was 10 µm in the longitudinal direction (X-axis direction in FIG. 1) in which the light-transmitting portion extends. The 3000 light-transmitting portions become a single filtration portion to be formed later. 10×10 filtration portions were arranged along a vertical direction and a horizontal direction. At this time, a connection portion was provided between the filtration portions adjacent to each other, and a width of the connection portion was set to 10 mm. The glass mask was placed on a photoresist lamination surface of the substrate. At this time, a surface side of the glass mask, in which the light-transmitting portions were provided, was set to face the photoresist lamination surface.

Next, a cancer cell-trapping metal filter according to Example 2 was prepared by the same method as Example 1. In the cancer cell-trapping metal filter that was completed, the photoresist patterns did not collapse during a manufacturing process, and damage such as a winkle, bending, a scratch, and curling was not present in the completed filter. The thickness of the cancer cell-trapping metal filter was 23 µm. In addition, the length of a short side of each connected through-hole was 7.6 µm on an upper surface side (on a short length side of the short side) of the cancer cell-trapping metal filter, and 7.8 µm on a lower surface side (on a long length side of the short side). In addition, the opening ratio of the cancer cell-trapping metal filter according to Example 2 was 26.7%.

Example 3

A photoresist (PHOTEC RD-1225 having a thickness of 25 µm, manufactured by Hitachi Chemical Co., LTD.) was laminated to a one surface of a substrate of 250 mm square (MCL-E679F: a substrate obtained by bonding peelable copper foil to a surface of MCL, manufactured by Hitachi Chemical Co., LTD.). The lamination was performed under conditions a rolling temperature of 90° C., a pressure of 0.3 MPa, a conveyor speed of 2.0 m/minute.

Next, a glass mask having the following configuration was prepared. In a single wave-shaped light-transmitting portion, eight light-transmitting portions having a rectangular shape with rounded corners in which a length of a short side was 9 µm and a length of a long side was 30 µm were continuously connected at ends. In addition, 100 pieces of the light-transmitting portions were arranged in the same direction along a short direction (Y-axis direction in FIG. 1) perpendicular to the longitudinal direction (X-axis direction in FIG. 1) in which the wave-shaped light-transmitting portion extends, and 100 rows of the light-transmitting portions were arranged along the longitudinal direction. An intersection angle of the light-transmitting portions, which are connected to be adjacent to each other and which have a rectangular shape with rounded corners, was 100°, and intersection directions between adjacent connected portions were different from each other. The shortest distance between adjacent light-transmitting portions was 11 µm in the short direction (Y-axis direction in FIG. 1) perpendicular to the longitudinal direction in which the light-transmitting portion extends, and was 10 µm in the longitudinal direction (X-axis direction in FIG. 1) in which the light-transmitting portion extends. The 10000 light-transmitting portions become a single filtration portion to be formed later. 10×10 filtration portions were arranged along a vertical direction and a horizontal direction. At this time, a connection portion was provided between the filtration portions adjacent to each other, and a width of the connection portion was set to 10 mm. The glass mask was placed on a photoresist lamination surface of the substrate. At this time, a surface side of the glass mask, in which the light-transmitting portions were provided, was set to face the photoresist lamination surface.

Next, a cancer cell-trapping metal filter as shown in FIG. 4 according to Example 3 was prepared by the same method as Example 1. In the cancer cell-trapping metal filter that was completed, the photoresist patterns did not collapse during a manufacturing process, and damage such as a winkle, bending, a scratch, and curling was not present in the completed filter. The thickness of the cancer cell-trapping metal filter was 23 µm. In addition, the length of a short side of each connected through-hole was 8.6 µm on an upper surface side (on a short length side of the short side) of the cancer cell-trapping metal filter, and 8.8 µm on a lower surface side (on a long length side of the short side). In addition, the opening ratio of the cancer cell-trapping metal filter according to Example 3 was 40.7%.

Examples 4 to 6

Gold plating of approximately 0.05 µm was performed on the surface of the cancer cell-trapping metal filters, which were prepared in Examples 1 to 3, by using a gold substitution plating solution HGS-500 (manufactured by Hitachi Chemical Co., Ltd.) according to a process shown in Table 2 under gold plating conditions shown in Table 3. According to this, cancer cell-trapping metal filters according to Examples 4 to 6 were obtained. In any example, in the cancer cell-trapping metal filter that is completed, the photoresist patterns did not collapse during a manufacturing process, and damage such as a winkle, bending, a scratch, and curling was not present in the completed filter. The opening ratio and the length of the short side of the connected through-holes on a filter upper surface side of the cancer cell-trapping metal filters according to Examples 4 to 6 are shown in Table 4.

TABLE 2

| Process | Treatment content |
|---|---|
| 1 | Acidic degreasing |
| 2 | Hot-water washing |
| 3 | Gold plating |
| 4 | Water washing |
| 5 | Pure-water washing |

TABLE 3

| Item | Condition |
|---|---|
| Gold concentration | 0.7 g/L |
| pH | 5-6 |
| Temperature | 85° C. |
| Time | 10 min. |

TABLE 4

| | Opening ratio | Length of short side on upper surface side of filter |
|---|---|---|
| Example 4 | 22.7% | 9.4 μm |
| Example 5 | 26.7% | 7.4 μm |
| Example 6 | 40.7% | 8.4 μm |

Comparative Example 1

A photoresist (PHOTEC RD-1225 having a thickness of 25 μm, manufactured by Hitachi Chemical Co., LTD.) was laminated to a one surface of a substrate of 250 mm square (MCL-E679F: a substrate obtained by bonding peelable copper foil to a surface of MCL, manufactured by Hitachi Chemical Co., LTD.). The lamination was performed under conditions a rolling temperature of 90° C., a pressure of 0.3 MPa, a conveyor speed of 2.0 m/minute.

Next, a glass mask having the following configuration was prepared.

Figure 14:
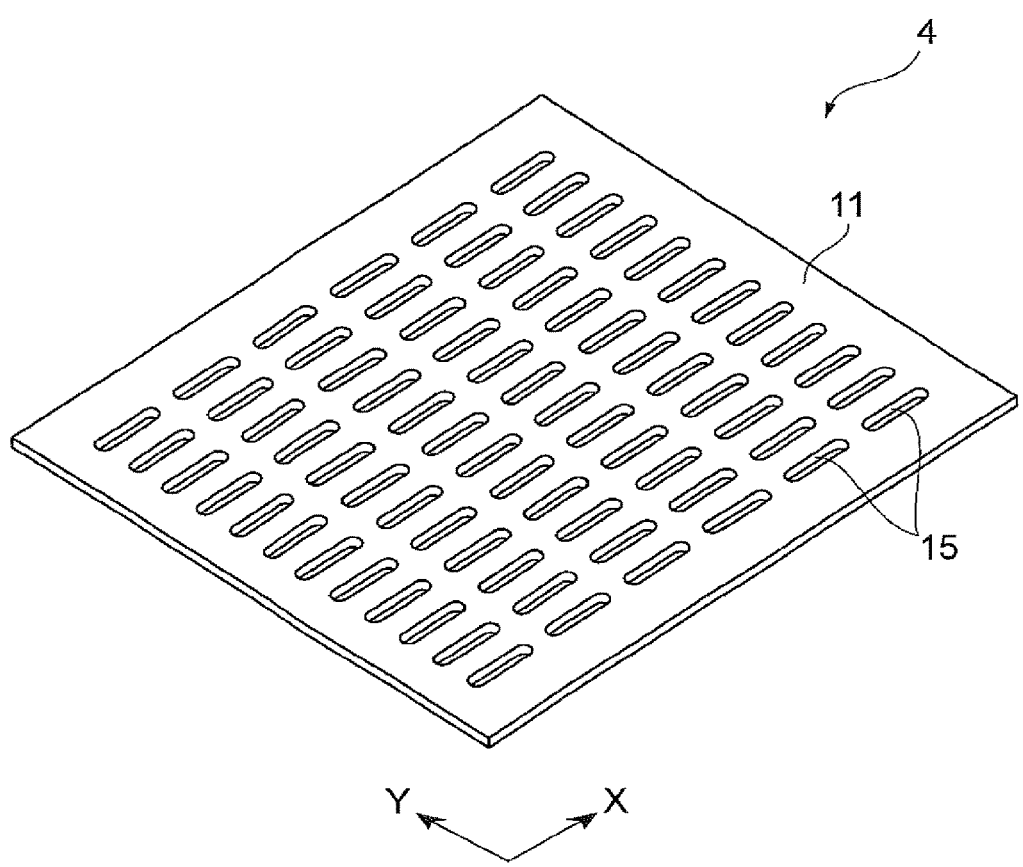
FIG. 14 is a schematic perspective view illustrating a configuration of a cancer cell-trapping metal filter according to Comparative Example 1.

Light-transmitting portions having a rectangular shape with rounded corners, in which a length of a short side was 8 μm and a length of a long side was 30 μm, were independently arranged as shown in FIG. 14. A glass mask, in which the shortest distance between adjacent light-transmitting portions was 12 μm in a short side direction and 10 μm in a long side direction, was prepared, and a cancer cell-trapping metal filter according to Comparative Example 1 was manufactured by the same method as Example 1. As shown in FIG. 14, in a cancer cell-trapping metal filter 4 according to Comparative Example 1, through-holes 15 having a rectangular shape with rounded corners are arranged along a predetermined direction. The photoresist was formed by the same method as Example 1, but the resist collapsed after development, and a plurality of detaching sites occurred. Due to this, leakage of the through-holes and arrangement collapse occurred, and thus the cancer cell-trapping metal filter 4 did not withstand practical use.

The cancer cell-tapping metal filters, which were manufactured in Examples 1 to 6, had a high opening ratio and were excellent in production efficiency. The cancer cell-trapping metal filter sheet, which is manufactured from the cancer cell-trapping metal filter on the basis of the above-described manufacturing method, can efficiently obtain the cancer cell-trapping metal filters in large quantities. In addition, the cancer cell-trapping device, which is manufactured by using the cancer cell-trapping metal filter on the basis of the above-described manufacturing method, can efficiently trap the CTC from the cell-containing body fluid, and the CTC that is trapped can be observed from the outside without disassembling the device.

REFERENCE SIGNS LIST 1, 1A, 1B, 1C, 1D: Cancer cell-trapping metal filter
2: Cancer cell-trapping metal filter sheet
3, 3': Cancer cell-trapping device
11: Metal sheet
12, 13, 14, 15, 16: Connected through-hole
17: Through-hole
21: Filtration portion
22: Connection portion
23: Positioning hole
31, 31': Cover member
32, 32': Accommodation member
301, 301': Inlet channel
302, 302': Outlet channel

The invention claimed is:

1. A method of manufacturing a cancer cell-trapping metal filter, comprising:
    laminating a photoresist on metal foil;
    overlapping a photomask including a wave-shaped light-transmitting portion on the photoresist and exposing the photoresist;
    removing an uncured portion of the photoresist by development to form photoresist patterns;
    performing metal plating between the photoresist patterns to form metal plating patterns having a height lower than a height of the photoresist patterns;
    removing the metal foil by chemical dissolution to obtain a structure including the metal plating patterns and the photoresist patterns; and
    removing the photoresist patterns from the structure to obtain the metal plating patterns having a through-hole corresponding to the light-transmitting portion.

2. The method of manufacturing a cancer cell-trapping metal filter according to claim 1,
    wherein the metal foil is adhered to a carrier layer, and the method further comprises peeling the carrier layer after forming the metal plating patterns.

3. The method of manufacturing a cancer cell-trapping metal filter according to claim 1,
    wherein an opening ratio of the through-hole is 10% to 50%.

4. The method of manufacturing a cancer cell-trapping metal filter according to claim 1, further comprising:
    plating a surface of the metal plating patterns with gold after obtaining the metal plating patterns.

5. A method of manufacturing a cancer cell-trapping device, comprising:
    providing the cancer cell-trapping metal filter according to claim 1 on a flow path inside a casing between an inlet channel and an outlet channel in such a manner that a hole diameter of the through-hole in a main surface of the cancer cell-trapping metal filter or on an upstream side becomes smaller than a hole diameter on a rear surface side of the cancer cell-trapping metal filter with respect to the main surface of the cancer cell-trapping metal filter, the casing including a cover member which is formed from a light-transmitting resin material and which has the inlet channel from which a liquid to be tested is introduced to the inside of the casing, and an accommodation member that includes the outlet channel through which the liquid to be tested is discharged to the outside of the casing.

6. The method of manufacturing a cancer cell-trapping device according to claim 5,
wherein the cover member and the accommodation member are welded to each other.

7. The method of manufacturing a cancer cell-trapping metal filter according to claim 1,
wherein the metal plating patterns are formed to have a plurality of through-holes.

8. The method of manufacturing a cancer cell-trapping metal filter according to claim 7,
wherein an opening ratio of the through-holes is 10% to 50%.

9. A method of manufacturing a cancer cell-trapping metal filter sheet, comprising:
laminating a photoresist on metal foil;
overlapping a photomask including a plurality of blocks of wave-shaped light-transmitting portions on the photoresist and exposing the photoresist;
removing an uncured portion of the photoresist by development to form photoresist patterns;
performing metal plating between the photoresist patterns to form metal plating patterns having a height lower than a height of the photoresist patterns;
removing the metal foil by chemical dissolution to obtain a structure including the metal plating patterns and the photoresist patterns; and
removing the photoresist patterns from the structure to obtain the metal plating patterns having a through-hole corresponding to the light-transmitting portion.

10. The method of manufacturing a cancer cell-trapping metal filter sheet according to claim 9,
wherein the metal foil is adhered to a carrier layer, and the method further comprises peeling the carrier layer after forming the metal plating patterns.

11. The method of manufacturing a cancer cell-trapping metal filter sheet according to claim 9,
wherein in overlapping the photomask on the photoresist and exposing the photoresist, a photomask, which includes a second light-transmitting portion different from the light-transmitting portion at the periphery of the blocks of the wave-shaped light-transmitting portions, is used.

12. The method of manufacturing a cancer cell-trapping metal filter sheet according to claim 9,
wherein an opening ratio of the through-hole is 10% to 50%.

13. The method of manufacturing a cancer cell-trapping metal filter sheet according to claim 9, further comprising:
plating a surface of the metal plating patterns with gold after obtaining the metal plating patterns.

14. The method of manufacturing a cancer cell-trapping metal filter according to claim 9,
wherein the metal plating patterns are formed to have a plurality of through-holes.

15. The method of manufacturing a cancer cell-trapping metal filter according to claim 14,
wherein an opening ratio of the through-holes is 10% to 50%.

\* \* \* \* \*